(12) United States Patent
Landrigan et al.

(10) Patent No.: US 8,728,008 B2
(45) Date of Patent: May 20, 2014

(54) BONE MARROW ASPIRATION NEEDLE

(75) Inventors: Matthew D. Landrigan, Fort Wayne, IN (US); James M. McKale, Leesburg, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 252 days.

(21) Appl. No.: 12/849,412

(22) Filed: Aug. 3, 2010

(65) Prior Publication Data

US 2012/0035501 A1 Feb. 9, 2012

(51) Int. Cl.
A61M 25/10 (2013.01)

(52) U.S. Cl.
USPC .......... 600/581; 600/562; 600/565; 600/566; 600/567; 600/576; 600/578; 600/579

(58) Field of Classification Search
USPC ......... 600/562, 565, 566, 567, 576, 578, 579, 600/581
See application file for complete search history.

(56) References Cited

U.S. PATENT DOCUMENTS

| | | | | |
|---|---|---|---|---|
| 5,061,257 A * | 10/1991 | Martinez et al. | 604/526 |
| 5,603,703 A * | 2/1997 | Elsberry et al. | 604/268 |
| 5,944,673 A * | 8/1999 | Gregoire et al. | 600/564 |
| 6,050,955 A * | 4/2000 | Bryan et al. | 600/566 |
| 6,165,199 A * | 12/2000 | Barbut | 606/200 |
| 6,394,973 B1 * | 5/2002 | Cucin | 604/22 |
| 6,488,636 B2 * | 12/2002 | Bryan et al. | 600/566 |
| 6,733,479 B1 * | 5/2004 | Ott | 604/264 |
| 6,981,949 B2 * | 1/2006 | Hibner et al. | 600/566 |
| 7,066,893 B2 * | 6/2006 | Hibner et al. | 600/566 |
| 7,179,232 B2 * | 2/2007 | Sutton et al. | 600/567 |
| 7,462,181 B2 | 12/2008 | Kraft et al. | |
| 7,510,535 B2 * | 3/2009 | Hibner et al. | 600/566 |
| 7,637,872 B1 | 12/2009 | Fox | |
| 7,727,164 B2 * | 6/2010 | Cicenas et al. | 600/564 |
| 7,914,461 B2 * | 3/2011 | Richard et al. | 600/562 |
| 7,918,804 B2 * | 4/2011 | Monson et al. | 600/568 |
| 8,123,699 B2 * | 2/2012 | Lyon | 600/567 |
| 2002/0007130 A1 * | 1/2002 | Burbank et al. | 600/564 |
| 2002/0193705 A1 * | 12/2002 | Burbank et al. | 600/562 |
| 2003/0009132 A1 * | 1/2003 | Schwartz et al. | 604/152 |
| 2003/0139688 A1 | 7/2003 | Lamoureux et al. | |
| 2003/0229292 A1 * | 12/2003 | Hibner et al. | 600/566 |
| 2003/0229293 A1 * | 12/2003 | Hibner et al. | 600/567 |
| 2004/0260200 A1 * | 12/2004 | Morello | 600/566 |
| 2004/0267154 A1 * | 12/2004 | Sutton et al. | 600/562 |
| 2006/0200041 A1 * | 9/2006 | Weikel et al. | 600/566 |

(Continued)

FOREIGN PATENT DOCUMENTS

GB 2130890 A 6/1984

OTHER PUBLICATIONS

International Search Report mailed Mar. 4, 2013 for PCT/US2012/070561 which claims benefit of U.S. Appl. No. 13/332,799, filed Dec. 21, 2011.

*Primary Examiner* — Sean Dougherty
(74) *Attorney, Agent, or Firm* — Harness, Dickey

(57) ABSTRACT

A bone marrow aspiration assembly including an outer cannula and an inner cannula. The inner cannula is moved only radially about a longitudinal axis thereof with respect to the outer cannula to selectively align inner openings of only one of distal, intermediate, and proximal opening groups of the inner cannula with outer openings of only one of distal, intermediate, and proximal opening groups of the outer cannula to permit aspiration therethrough.

15 Claims, 25 Drawing Sheets

(56) References Cited

U.S. PATENT DOCUMENTS

| | | |
|---|---|---|
| 2006/0200042 A1* | 9/2006 | Weikel et al. ............... 600/566 |
| 2006/0241516 A1* | 10/2006 | Hibner et al. .............. 600/566 |
| 2007/0066987 A1 | 3/2007 | Scanlan et al. |
| 2007/0198043 A1 | 8/2007 | Cox et al. |
| 2007/0219460 A1 | 9/2007 | Goldenberg |
| 2007/0276352 A1 | 11/2007 | Crocker et al. |
| 2007/0293788 A1 | 12/2007 | Entrekin et al. |
| 2008/0058674 A1* | 3/2008 | Jansen et al. ............... 600/567 |
| 2008/0119759 A1 | 5/2008 | McLain |
| 2009/0131827 A1 | 5/2009 | Crocker et al. |
| 2009/0187116 A1 | 7/2009 | Noishiki et al. |
| 2009/0204024 A1 | 8/2009 | Miller |
| 2010/0063416 A1* | 3/2010 | Cicenas et al. ............... 600/567 |
| 2012/0035501 A1* | 2/2012 | Landrigan et al. ............ 600/567 |
| 2012/0129676 A1* | 5/2012 | Duffy et al. .................... 494/37 |
| 2012/0136277 A1 | 5/2012 | Landrigan et al. |
| 2012/0316513 A1* | 12/2012 | Sharkey et al. ............... 604/256 |

* cited by examiner

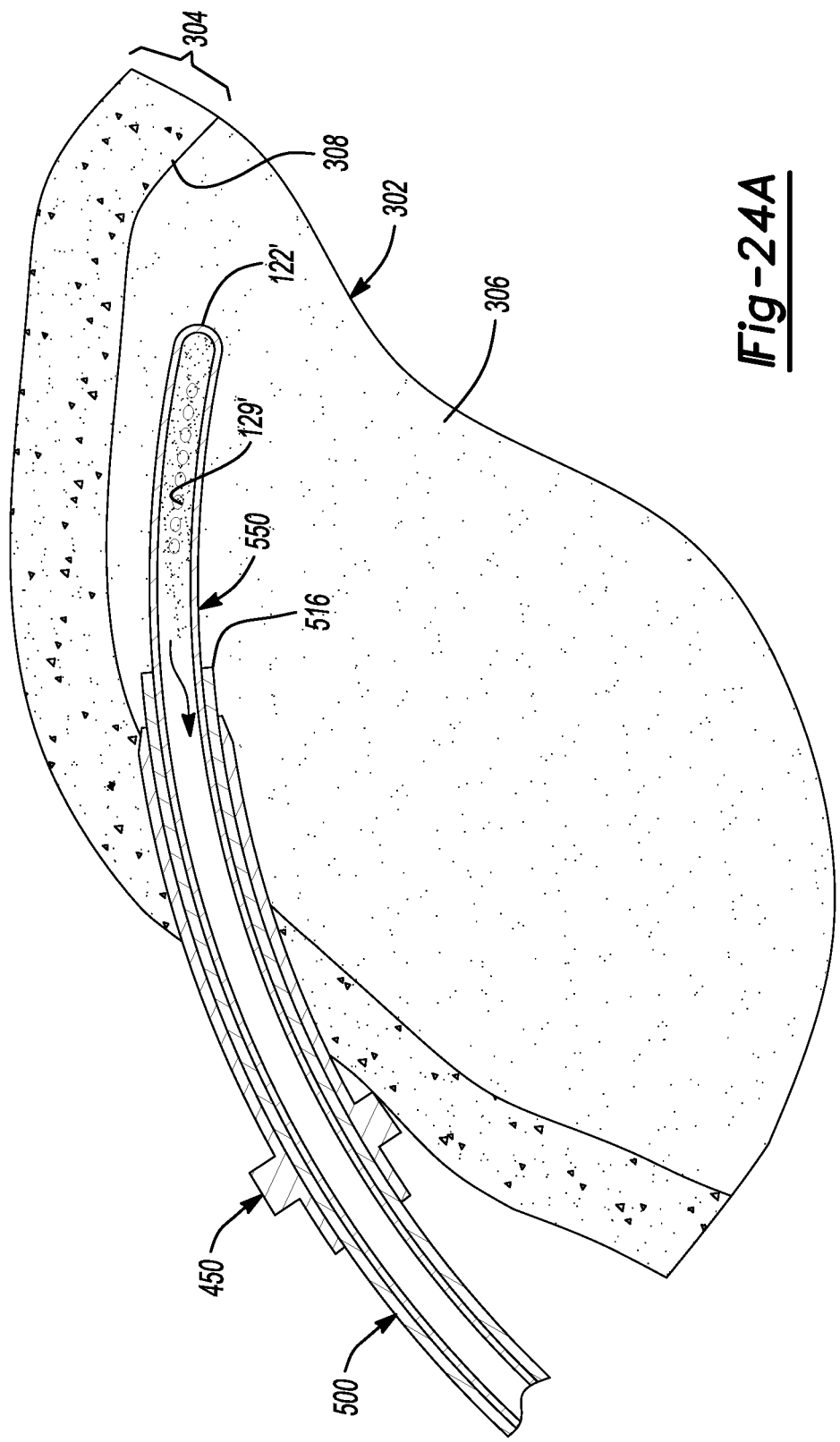

BONE MARROW ASPIRATION NEEDLE

FIELD

The present disclosure relates to bone marrow aspiration needles.

BACKGROUND

This section provides background information related to the present disclosure which is not necessarily prior art.

Autologous stem cell therapies often utilize a patient's bone marrow or concentrated bone marrow aspirate to deliver autologous adult mononuclear stem cells to the patient for the treatment of a wide variety of disorders. Concentrated autologous cell therapies utilize in vitro cell culture to expand a desired cell line, or a point-of-care device to concentrate the mononuclear cell-rich fraction (CRF), for delivery to a desired treatment site. An exemplary point-of-care device is the MarrowStim™ device by Biomet Biologics, LLC of Warsaw, Ind.

Concentration of the mononuclear CRF is limited by the number of recovered mononuclear cells in the aspirate. Often, aspiration of four 1 ml aspirates recovers almost twice the number of osteoblast progenitor cells as compared to a single 4 ml aspirate. This discrepancy is often attributed to aspirate dilution from peripheral blood. Harvesting smaller volumes of aspirate from a variety of different locations, such as along the curved iliac crest of the pelvis, can improve the baseline and concentrated mononuclear CRF, which will lead to more effective stem cell therapies.

SUMMARY

This section provides a general summary of the disclosure, and is not a comprehensive disclosure of its full scope or all of its features.

The present teachings provide for a bone marrow aspiration assembly including an outer cannula and an inner cannula. The outer cannula extending along a first longitudinal axis and including a first outer surface and a first inner surface. The first inner surface defining a first passageway extending along the first longitudinal axis. The outer cannula defining a plurality of outer openings that are in communication with the first passageway, extend between the first inner and first outer surfaces of the outer cannula, and are arranged in distal, intermediate, and proximal groups along the first longitudinal axis. The inner cannula extends along a second longitudinal axis that is configured to be received in the first passageway. The inner cannula includes a second outer surface and a second inner surface. The second inner surface defining a second passageway extending along the second longitudinal axis. The inner cannula defining a plurality of inner openings that are in communication with the second passageway, that extend between the second inner and second outer surfaces of the inner cannula, and are arranged in distal, intermediate, and proximal groups along the second longitudinal axis. The inner cannula is moved only radially about the second longitudinal axis with respect to the outer cannula to selectively align the inner openings of only one of the distal, intermediate, and proximal opening groups of the inner cannula with the outer openings of only one of the distal, intermediate, and proximal opening groups of the outer cannula to permit aspiration therethrough.

The present teachings also provide for a bone marrow aspiration assembly including a cannulated bone piercing needle, a cannulated introducer needle, and a flexible aspiration needle. The cannulated introducer needle is curved to approximate a natural curvature of an iliac crest. The introducer needle has a length longer than the piercing needle and is configured to be received within, and pass through, the piercing needle. The flexible aspiration needle has apertures for aspirating bone marrow and is configured to be received in, and extend from, the cannulated introducer needle to reach a bone marrow aspiration site.

The present teachings further provide for a bone marrow aspiration assembly including a flexible outer cannula and a flexible inner cannula. The flexible outer cannula defines a first passageway and includes a plurality of first ports between a first end and a second end of the first passageway. The flexible inner cannula defines a second passageway and is configured to be received within the first passageway. The flexible inner cannula includes a plurality of second ports between a first end and a second end of the second passageway. The flexible inner cannula is longitudinally and axially movable relative to the flexible outer cannula to simultaneously selectively align at least one first port with at least one second port to permit aspiration of bone marrow there through and to misalign at least one first port and at least one second port to restrict aspiration of bone marrow there through Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 20A is another distal tip that may be provided with the outer needle assembly of FIG. 20;

FIG. 24A is similar to FIG. 24, but with the flexible needle including a plurality of circular openings.

Corresponding reference numerals indicate corresponding parts throughout the several views of the drawings.

DETAILED DESCRIPTION

Example embodiments will now be described more fully with reference to the accompanying drawings.

Figure 1:
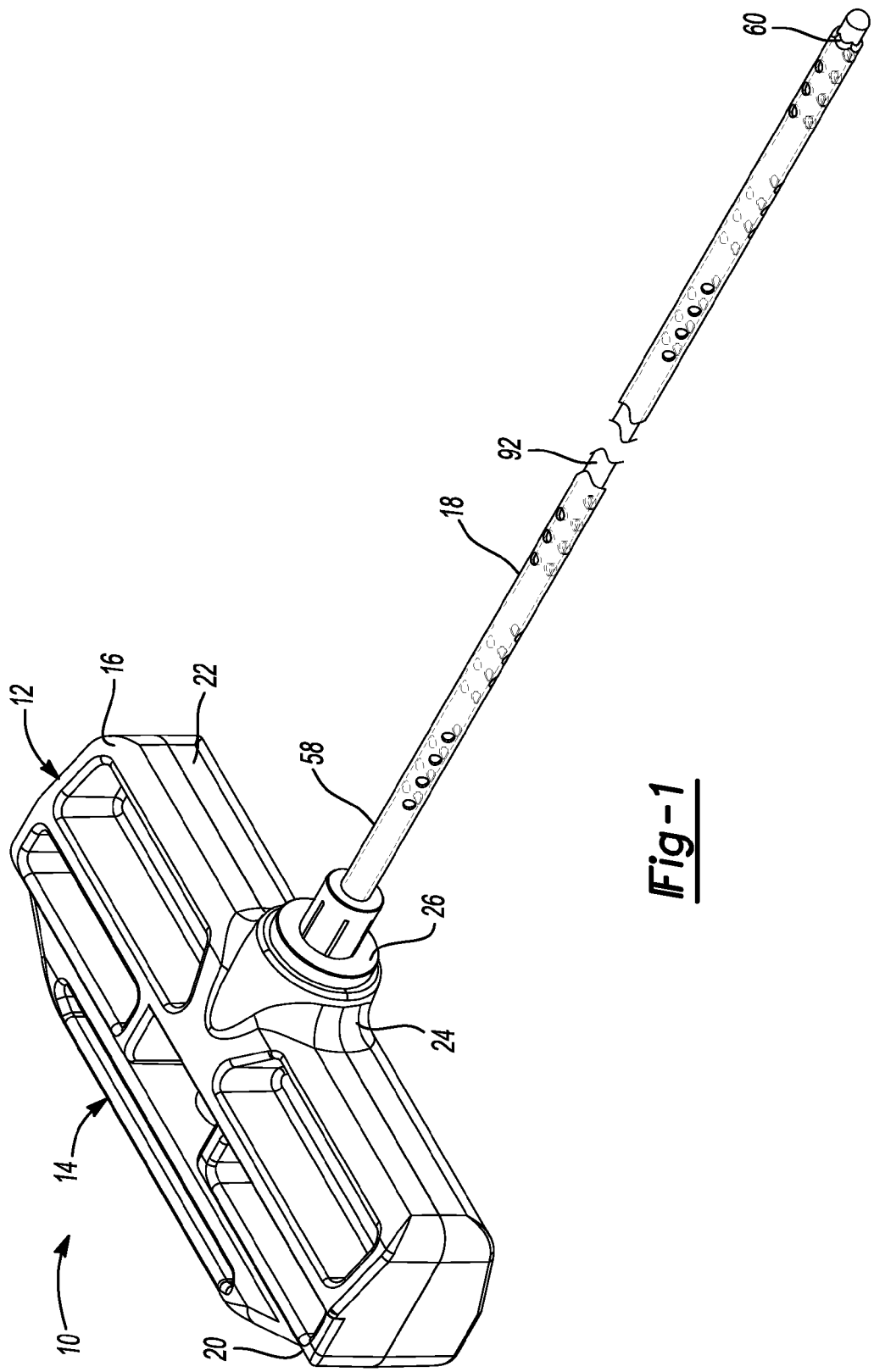
FIG. 1 is a perspective view of a bone marrow aspiration assembly according to the present teachings.
Figure 2:
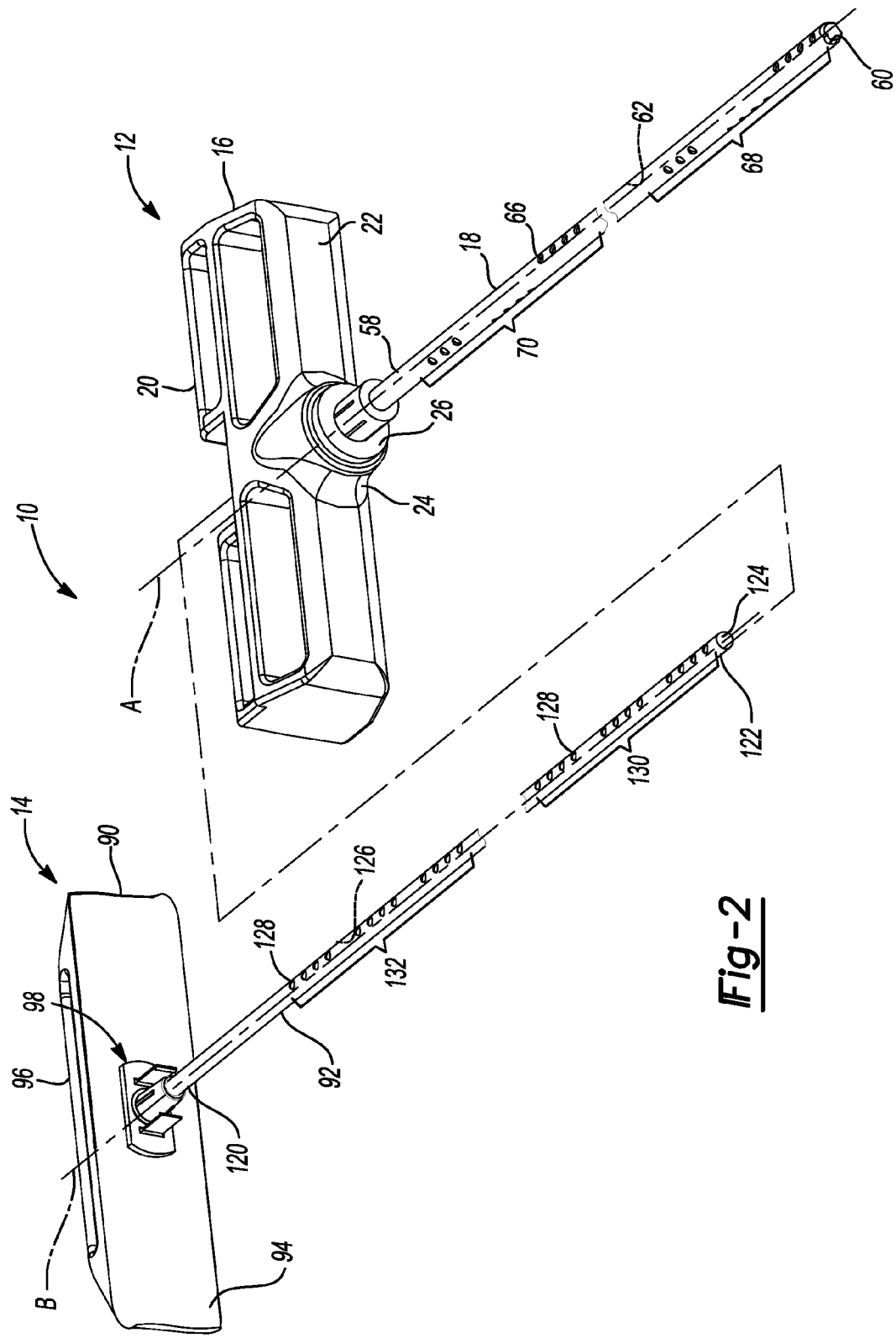
FIG. 2 illustrates an inner needle assembly separated from an outer needle assembly of the bone marrow aspiration assembly of FIG. 1.

With initial reference to FIG. 1 and FIG. 2, a bone marrow aspiration assembly according to the present teachings is generally illustrated at reference numeral 10. The assembly 10 generally includes an outer needle assembly 12 and an inner needle assembly 14.

The outer needle assembly 12 includes an outer handle 16 and an outer cannula 18 extending therefrom. With additional reference to FIG. 3 and FIG. 3A, the outer handle 16 includes a proximal surface 20 and a distal surface 22 opposite to the proximal surface 20. The distal surface 22 has a raised neck 24 at a center thereof. The raised neck 24 includes a distal portion 26.

Figure 3:
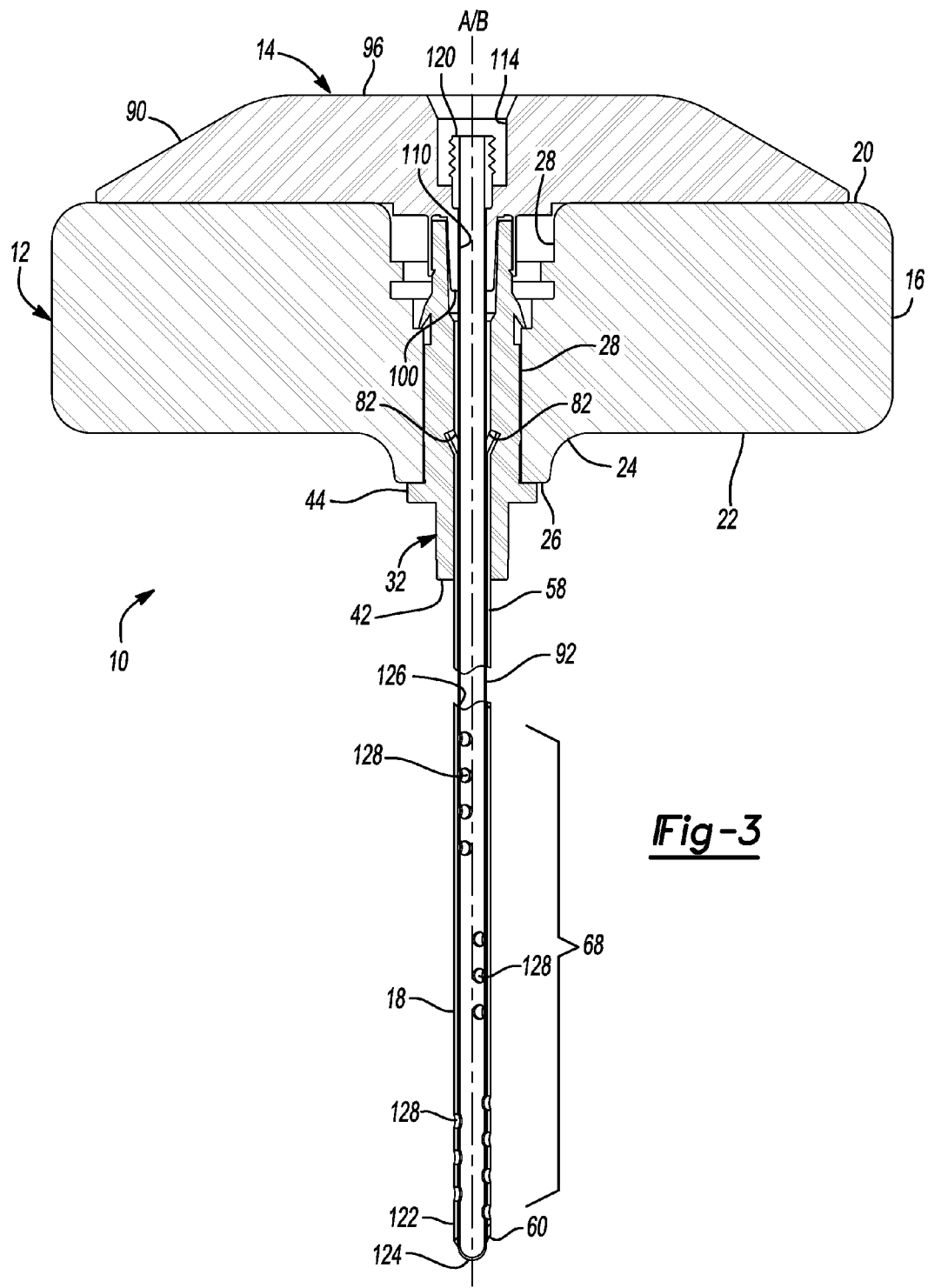
FIG. 3 is a cross-sectional view of the bone marrow aspiration assembly.
Figure 3A:
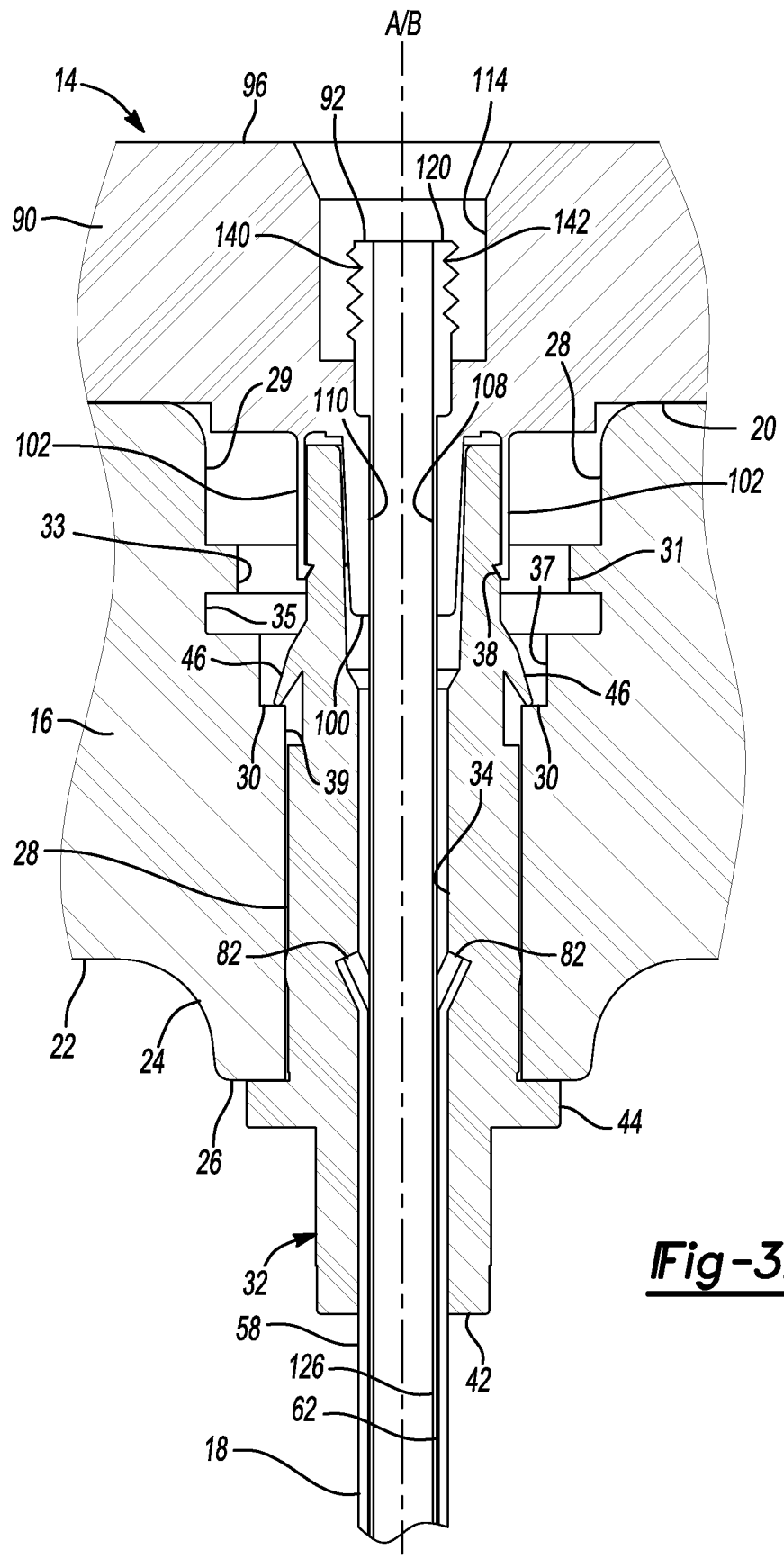
FIG. 3A is an enlarged cross-sectional view of the bone marrow aspiration assembly showing cooperation between the inner needle assembly and the outer needle assembly.

With reference to FIGS. 3 and 3A, the outer handle 16 defines a through bore 28 extending between the proximal surface 20 and a center of the distal portion 26 of the raised neck 24. A longitudinal axis A extending through an axial center of the through bore 28 is perpendicular to each of a plane extending across the proximal surface 20, a plane extending across the distal surface 22, and a plane extending across the distal portion 26 of the raised neck 24.

With reference to FIG. 3A, at approximately a mid-point of the through bore 28, the outer handle 16 defines a stepped, annular retention surface 30. Between the retention surface 30 and the proximal surface 20 is an annular flange 31 protruding into the through bore 28 toward the longitudinal axis A. The outer handle 16 defines a plurality of diameter areas of the through bore 28 having diameters of various sizes.

A first area 29 is between the proximal surface 20 and the flange 31. From the proximal surface 20, the first area 29 tapers inward toward the longitudinal axis A, and retains a generally uniform diameter about the longitudinal axis A as it extends in the distal direction (toward the distal surface 22) until it reaches the flange 31. A second area 33 is at the flange 31. The second area 33 has a diameter that is smaller than the diameter of the first area 29. A third area 35 is adjacent to the flange 31 on a distal side thereof (closest to the distal surface 22). The third area 35 has a diameter that is similar in size to the diameter of the first area 29. A fourth area 37 is between the annular retention surface 30 and the third area 35. A fifth area 39 is between the annular retention surface 30 and the distal portion 26 of the neck 24. The fifth area 39 has the smallest diameter, which is generally uniform throughout its length. The fourth area 37 has a diameter that is greater than the diameter of the fifth area 39, but smaller than the diameter of the second area 33.

Figure 4:
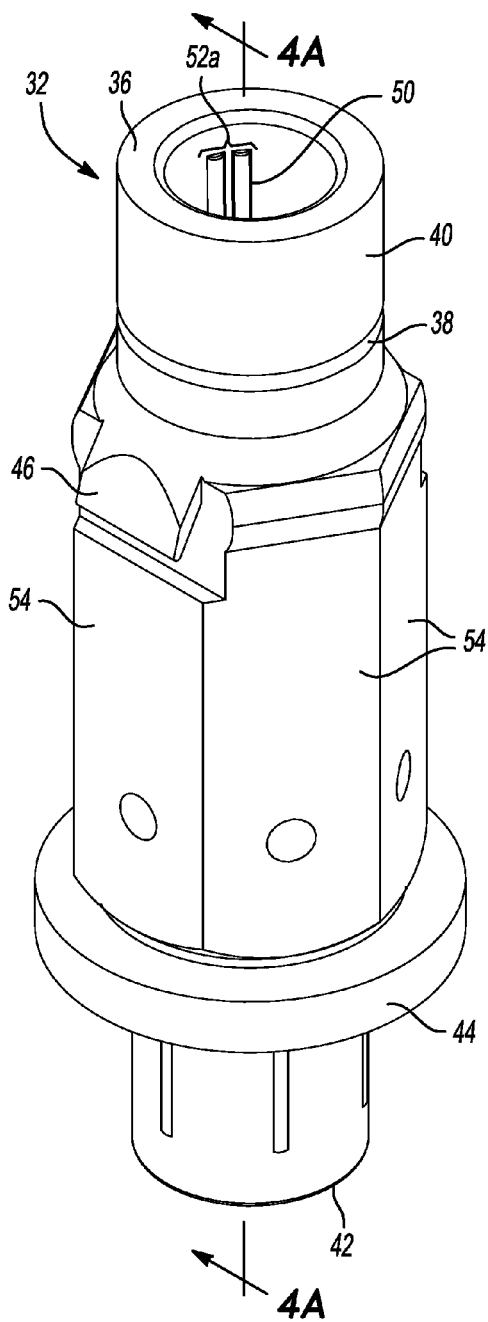
FIG. 4 is a perspective view of an insert of the outer needle assembly.
Figure 4A:
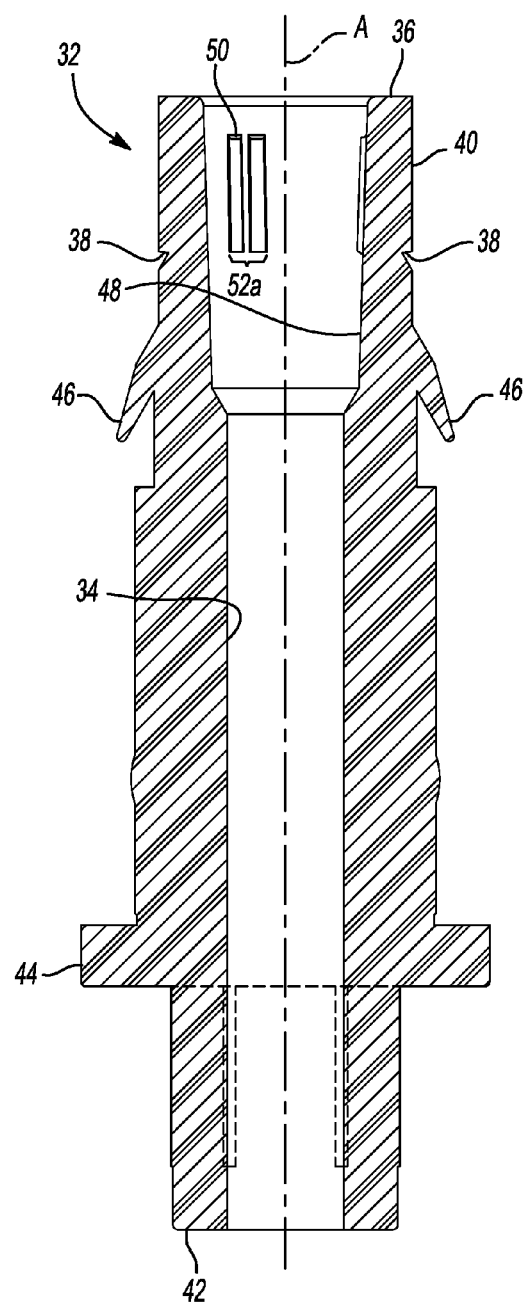
FIG. 4A is a cross-sectional view of the insert of FIG. 4.

With additional reference to FIGS. 4 and 4A, an insert 32 is seated within the through bore 28. The insert 32 defines a center channel 34 having a longitudinal axis that is common with the longitudinal axis A. Near a proximal end 36 of the insert 32, but spaced apart therefrom, is an annular recess 38 extending around an outer surface 40 of the insert 32. Proximate to a distal end 42 of the insert 32, but spaced apart therefrom, is an annular collar 44 extending from the insert 32 in a direction perpendicular to the longitudinal axis A. Between the annular recess 38 and the annular collar 44, but closer to the annular recess 38, is a pair of flexible retention fins 46.

The diameter of the center channel 34 is greatest at a portion 48 that is at the proximal end 36. The diameter of the center channel 34 tapers inward from the proximal end 36 to a point along the length of the center channel 34 that is approximately even with the fins 46. The remainder of the center channel 34, which extends along the longitudinal axis A to the distal end 42 has a generally uniform diameter.

Figure 5:
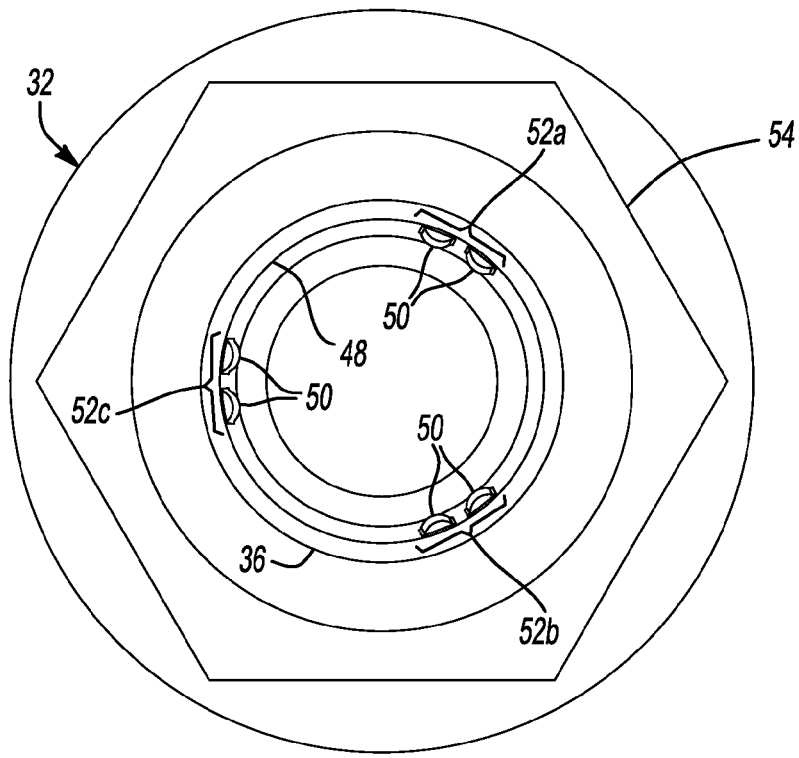
FIG. 5 is a top view of the insert.

With additional reference to FIG. 5, protruding from a portion of the insert 32 defining the large diameter portion 48 of the center channel 34 are a series of raised surfaces or bumps 50. A first pair 52a, a second pair 52b, and a third pair 52c of the bumps 50 are arranged at 120° intervals around the large diameter portion 48. The two bumps 50 of each pair 52a, 52b, and 52c are spaced apart to securely receive a portion of the inner handle 90 therebetween, as described herein. FIGS. 4 and 5 also illustrate six planar surfaces 54 of the outer surface 40, which are in a hexagonal arrangement and are between the collar 4 and the fins 46. The planar surfaces 54 restrict rotational movement of the insert 32 about the longitudinal axis A when seated in the through bore 28.

Figure 6:
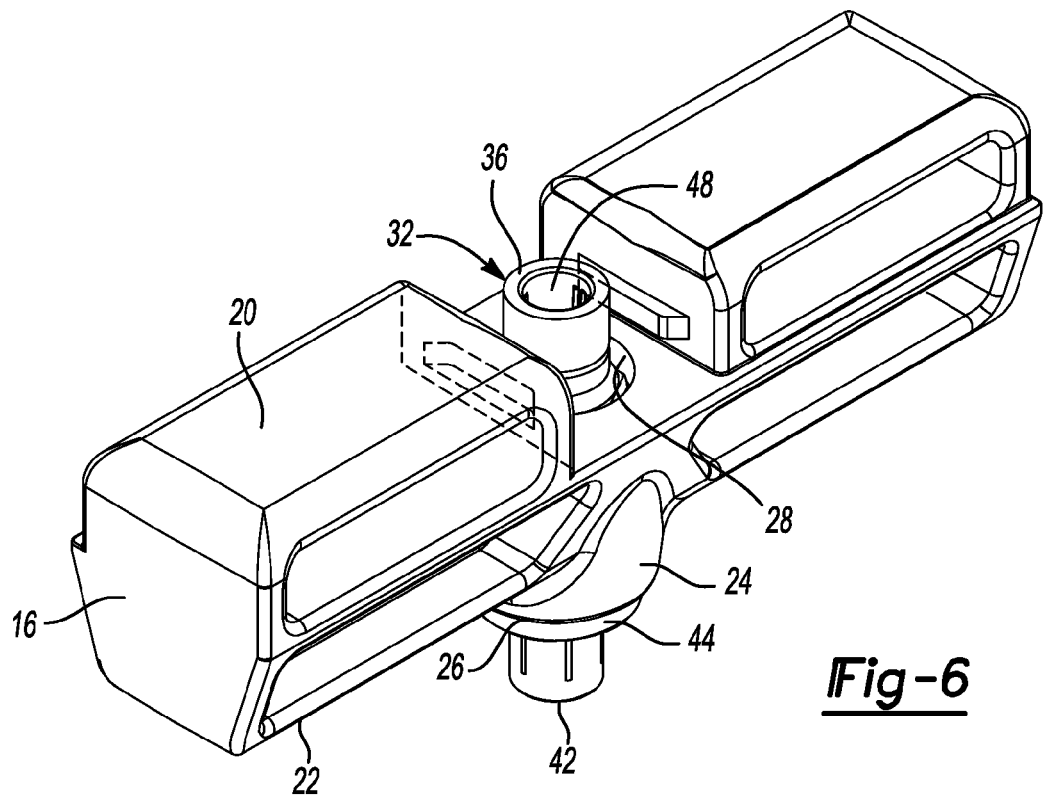
FIG. 6 is a perspective view of a handle of the outer needle assembly.

As illustrated in FIGS. 3A and 6 for example, the insert 32 is positioned within the through bore 28 of the handle 16 such that the proximal end 36 is at, or closely proximate to, the plane extending across the proximal surface 20 of the outer handle 16 and such that the distal end 42 extends beyond the distal portion 26 of the raised neck 24. The collar 44 abuts the distal portion 26 of the raised neck 24 and the fins 46 are seated on the retention surface 30. The handle 16 can be manufactured such that the insert 32 is a separately formed component that is inserted into the through bore 28 at the distal portion 26 until the annular, flexible fins 46 pass across the annular retention surface 30, at which point they expand from a contracted or first position to an expanded or second position to contact the annular retention surface 30. The collar 44 and the flexible fins 46 retain the insert 32 within the through bore 28.

Alternatively, the handle 16 can be manufactured such that the insert 32 is molded together with the remainder of the handle 16 or the insert 32 can be formed integral with the remainder of the handle 16 during manufacturing. The handle 16 and the insert 32 may also be manufactured in any other suitable manner. Both the handle 16 and the insert 32 can be made of any suitable material, such as a suitable polymer.

With reference to FIGS. 2 and 3 for example, the outer cannula 18 includes a proximal end 58 and a distal end 60 and defines an outer cannula passageway 62 that extends an entire length of the outer cannula 18, from the proximal end 58 to the distal end 60. A longitudinal axis A extending through an axial center of the outer cannula passageway 62 is aligned with the longitudinal axis A of the through bore 28 (see FIG. 3); thus the longitudinal axis of the outer cannula passageway 62 is also designated with reference letter A.

Figure 7:
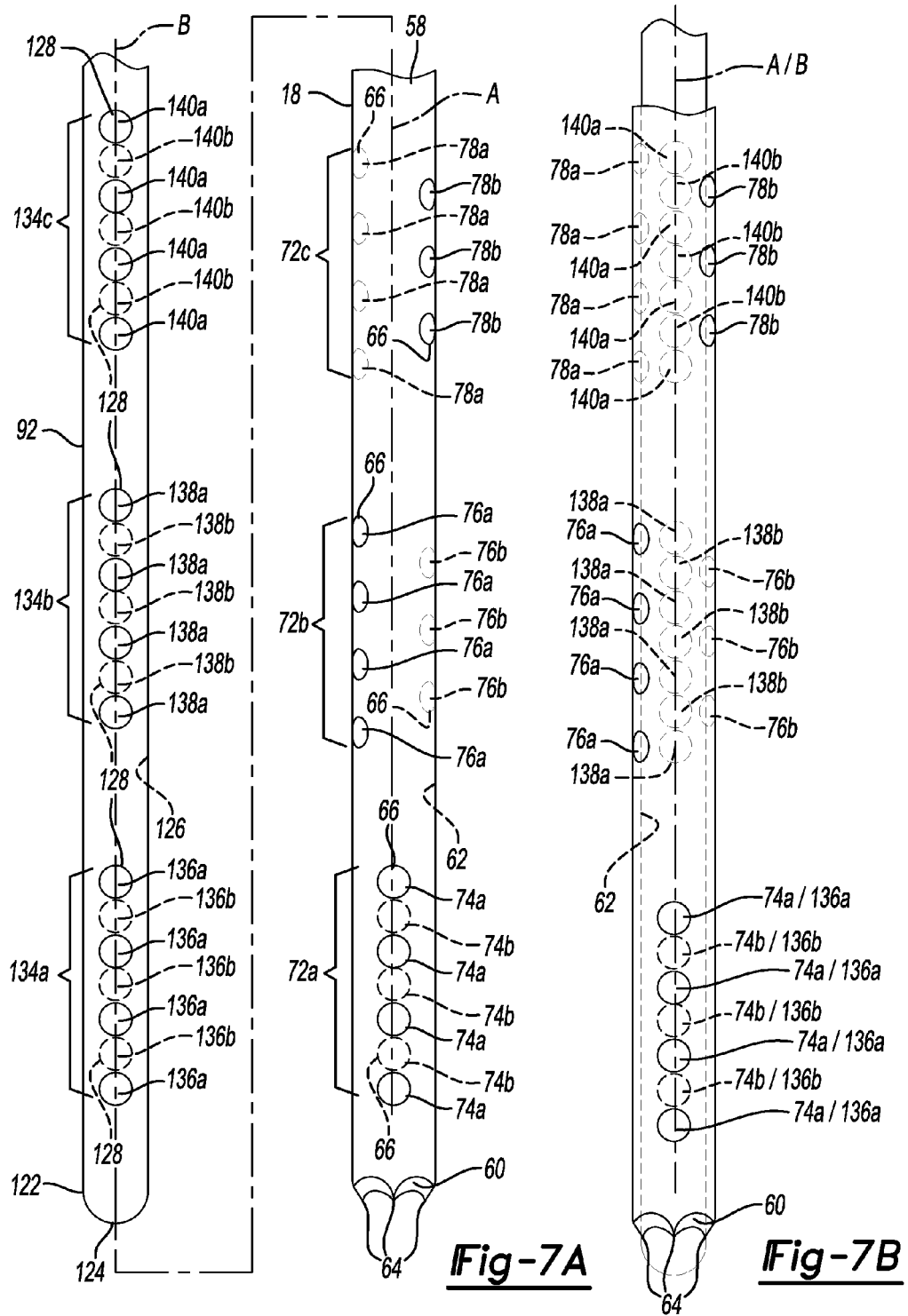
FIG. 7A illustrates a distal end of each of an outer cannula (right side of Figure) and an inner cannula (left side of Figure) of the bone marrow aspiration assembly.
FIG. 7B illustrates the inner cannula seated within the outer cannula.

With additional reference to FIG. 7A, the distal end 60 is open and includes a plurality of sharpened edges or teeth 64. The outer cannula 18 defines a plurality of openings 66 between the distal end 60 and the proximal end 58. The openings 66 provide communication between the passageway 62 and an exterior of the outer cannula 18.

As illustrated in FIG. 2, an outer distal set 68 and an outer proximal set 70 of the openings 66 are provided. Each of the outer distal set 68 and the outer proximal set 70 include multiple openings 66 spaced apart along the longitudinal axis A of the outer cannula 18. The outer distal set 68 is substantially similar to the outer proximal set 70. The description of the outer distal set 68 below is therefore also sufficient to describe the outer proximal set 70. Only one of the outer distal set 68 and the outer proximal set 70 may be provided in some applications. Additional sets of the openings 66 may also be included.

With specific reference to FIG. 7A, the outer distal set 68 will now be described. The outer distal set 68 includes an outer distal opening group 72a, an outer intermediate opening group 72b, and an outer proximal opening group 72c. The different outer opening groups 72a, 72b, and 72c are not radially aligned, but rather radially offset 120° from each other about axis A.

The outer distal opening group 72a includes a first distal array 74a of openings 66 and a second distal array 74b of openings 66. The first and the second distal arrays 74a and 74b are spaced 180° apart about the radius of the outer cannula 18. Each of the first and the second distal arrays 74a and 74b include a plurality of the openings 66 aligned parallel to the longitudinal axis A in the distal-to-proximal direction. The first distal array 74a includes four of the openings 66 and the second distal array 74b includes three of the openings 66. None of the openings 66 of the first distal array 74a are aligned in the distal to proximal direction with any of the openings 66 of the second distal array 74b, but rather the openings 66 are spaced apart.

The intermediate opening group 72b includes a first intermediate array 76a of openings 66 and a second intermediate array 76b of openings 66, which are each substantially similar to the first and the second distal arrays 74a and 74b respectively. The only substantial difference between the intermediate opening group 72b and the distal opening group 72a is that the first and the second intermediate arrays 76a and 76b are each radially rotated or shifted approximately 120° about the longitudinal axis A as compared to the first and the second distal arrays 74a and 74b.

The proximal opening group 72c includes a first proximal array 78a of openings 66 and a second proximal array 78b of openings 66. The first proximal array 78a is substantially similar to both the first intermediate array 76a and the first distal array 74a. The second proximal array 78b is substantially similar to both the second intermediate array 76b and the second distal array 74b. The only substantial difference between the proximal opening group 72c and both the intermediate opening group 72b and the distal opening group 72a is that the first and the second proximal arrays 78a and 78b are each radially rotated or shifted approximately 120° about the longitudinal axis A such that the first and the second proximal arrays 78a and 78b are not radially aligned with either the first and the second intermediate arrays 76a and 76b or the first and the second distal arrays 74a and 74b.

Figure 8:
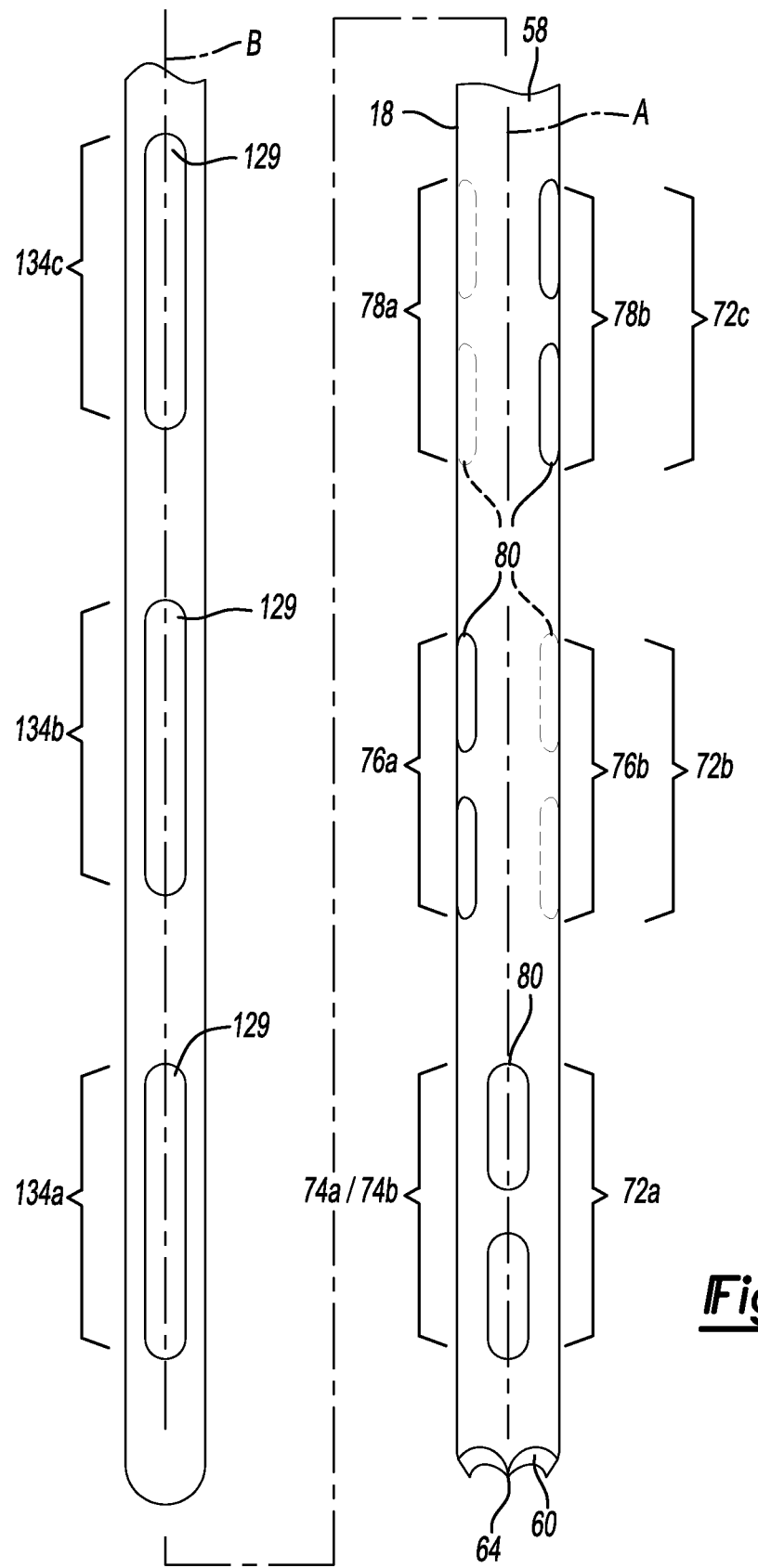
FIG. 8 illustrates a distal end of each of another outer cannula (right side of Figure) and another inner cannula (left side of Figure) according to the present teachings.

With additional reference to FIG. 8, the outer cannula 18 can alternatively include elongated slots 80, instead of the openings 66, which each extend parallel to the longitudinal axis A. Each of the arrays 74a, 74b (obscured behind array 74a in FIG. 8), 76a, 76b, 78a, and 78b include two slots 80 that are radially aligned with each other. The slots 80 of each of the first arrays 74a, 76a, and 78a are aligned with the slots 80 of each of the corresponding second arrays 74b, 76b, and 78b such that they overlap along the longitudinal axis A. The distal opening group 72a, the intermediate opening group 72b, and the proximal opening group 72c are each orientated such that the slots 80 of the different opening groups 72a, 72b, and 72c are not radially aligned, but rather offset by 120° degrees each as illustrated. This offset can also be 180°.

With reference to FIGS. 3 and 3A, the proximal end 58 of the outer cannula 18 includes a pair of opposing flared surfaces 82 that extend outward and away from the longitudinal axis A. At least a portion of the proximal end 58, including the flared surfaces 82, is seated within the insert 32 to mount the outer cannula 18 to the outer handle 16 by way of the insert 32. The flared surfaces 82 extend within the portion of the insert 32 defining the center channel 34 to secure the outer cannula 18 to the insert. The outer cannula 18 may also be secured to the insert 32 with a suitable adhesive or the insert 32 can be molded to the outer cannula 18 during manufacturing. The outer cannula passageway 62 is aligned with the center channel 34 of the insert 32 to provide a continuous passage from the proximal surface 20 of the handle 16 to the distal end 60 of the outer cannula 18.

The outer cannula 18 can be made of any suitable polymer or metal and can be rigid or flexible, as further discussed herein. For example, rigid stainless steel can be used, as well as flexible material, such as Nitinol.

Figure 9:
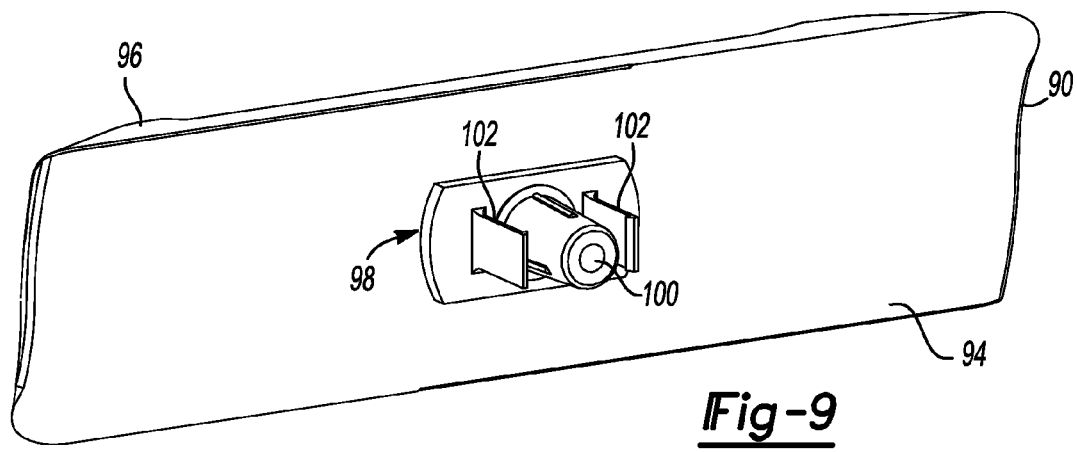
FIG. 9 is a perspective view of a distal side of a handle of the inner needle assembly.
Figure 9A:
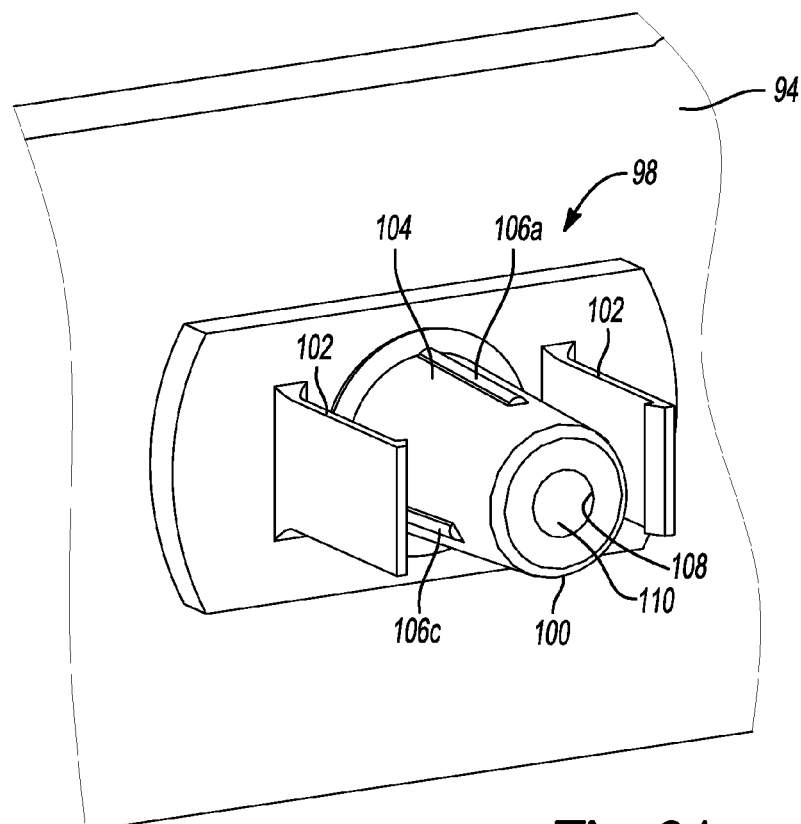
FIG. 9A is a perspective view of a connection region of the handle of the inner needle assembly.
Figure 9B:
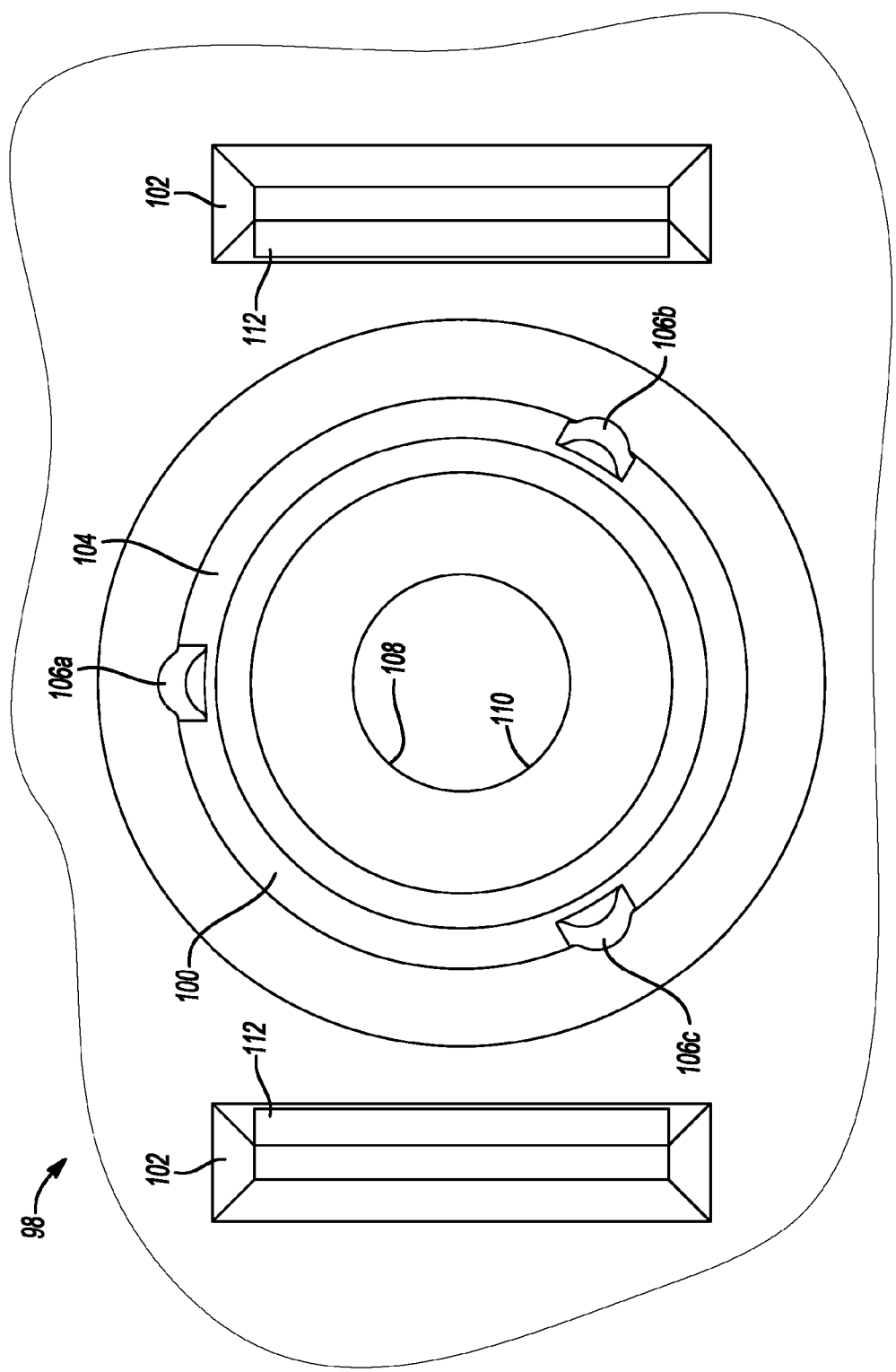
FIG. 9B is a planar view of a distal end of the connection region.

With reference to FIG. 2, the inner needle assembly 14 generally includes an inner handle 90 and an inner cannula 92 that extends from the inner handle 90 along longitudinal axis B. The inner handle 90 includes a distal surface 94 and a proximal surface 96 that is opposite to the distal surface 94. With continued reference to FIG. 2 and additional reference to FIGS. 9, 9A, and 9B, the distal surface 94 includes a connection region 98 at a center thereof. The connection region 98 includes a connection cone 100 between two connection tabs 102.

The connection cone 100 has a tapered outer surface 104 that is tapered in the proximal to distal direction such that a diameter of the outer surface 104 is greatest at the distal surface 94. Extending from the tapered outer surface 104 is a first ridge 106a, a second ridge 106b, and a third ridge 106c that are each positioned at 120° intervals about the outer surface 104 of the cone 100. The ridges 106 are elongated and extend along a portion of a length of the outer surface 104. An inner surface 108 of the connection cone 100 defines an inner connection channel 110 that extends through the connection cone 100. The inner surface 108 is cylindrical and has a generally uniform diameter throughout, which provides the inner connection channel 110 with a uniform diameter.

The connection tabs 102 each terminate at a tooth 112. The teeth 112 extend from their respective connection tabs 102 towards each other and oppose each other. The teeth 112 are sized to be received within the annular recess 38 of the insert 32.

The inner connection channel 110 is aligned along the longitudinal axis B with, and in communication with, a syringe receptacle 114 defined by the inner handle 90, as illustrated in FIG. 3A for example. The receptacle 114 extends from the proximal surface 96 and into a portion of the inner handle 90. The receptacle 114 has an inner diameter that is greatest at the proximal surface 96 of the inner cannula handle 90. From the proximal surface 96, the inner diameter of the syringe receptacle 114 tapers inward toward the longitudinal axis B, which is at an axial center of the syringe receptacle 114 and is co-linear with the longitudinal axis A when the inner needle assembly 14 is in cooperation with the outer needle assembly 12, as illustrated in FIGS. 3 and 3A.

The inner cannula 92 includes a proximal end 120 extending to the receptacle 114 and a distal end 122 that terminates at a closed tip 124. The inner cannula 92 defines an inner cannula passageway 126, as illustrated in FIGS. 3 and 3A, for example. The longitudinal axis B extends through an axial center of the inner cannula passageway 126. Between the proximal end 120 and the distal end 122 of the inner cannula 92 are a plurality of openings or ports 128, which provide communication between the inner cannula passageway 126 and an exterior of the inner cannula 92. As illustrated in FIG. 2, the openings 128 are arranged in an inner distal set 130 and an inner proximal set 132. The inner distal set 130 is substantially similar to the inner proximal set 132 and thus the below description of the inner distal set 130 also describes the inner proximal set 132. As with the outer distal and proximal sets 68 and 70, only one of the inner sets 130 and 132 need be provided, or additional inner sets of the openings 128 can be provided depending on the application. The number of sets of openings 128 provided will generally correspond to the number and sets of openings 66 provided.

With reference to FIG. 7A, the inner distal set 130 includes an inner distal opening group 134a, an inner intermediate opening group 134b, and an inner proximal opening group 134c. Unlike the outer opening groups 72a, 72b, and 72c of the outer distal set 68, the inner opening groups 134a, 134b, and 134c are all radially aligned along the longitudinal axis B.

The inner distal opening group 134a includes a first inner distal array 136a of openings 128 and a second inner distal array 136b of openings 128. The first inner distal array 136a is radially spaced apart 180° from the second inner distal array 136b. The first inner distal array 136a is substantially similar to the first outer distal array 74a of openings 66. The second inner distal array 136b is substantially similar to the second outer distal array 74b. Thus, the first inner distal array 136a includes four openings 128 radially aligned and spaced apart along a line parallel to the longitudinal axis B and the second inner distal array 136b includes three openings 128 that are radially aligned and spaced apart along a line parallel to the longitudinal axis B. The openings 128 of the first inner distal array 136a and the openings 128 of the second inner distal array 136b are not aligned in the distal to proximal direction, but rather staggered such that the openings 128 of the second inner distal array 136b are between the openings 128 of the first inner distal array 136a in the distal to proximal direction of the inner cannula 92.

The inner intermediate opening group 134b and the inner proximal opening group 134c are radially aligned with, and are substantially similar to, the inner distal opening group 134a, but spaced apart from the inner distal opening group 134a along the longitudinal axis B. Therefore, the description of the inner distal opening group 134a is also sufficient to describe both the inner intermediate opening group 134b and the inner proximal opening group 134c.

As illustrated in FIG. 3A, the proximal end 120 of the inner cannula 92 includes a syringe connector 140 having external threads 142. The syringe connector 140 may have any configuration suitable to couple a syringe to the inner cannula 92 in order to aspirate material there through, such as bone marrow, as further described herein.

The inner cannula 92 can be made of a suitable polymer or metal and can be rigid or flexible. For example, rigid stainless steel can be used, as well as flexible material, such as Nitinol.

As illustrated in FIG. 8, in place of the circular openings 128 the inner cannula 92 can include openings 129 shaped as elongated slots extending parallel to the longitudinal axis B. Each inner opening group 134a, 134b, and 134c can include a pair of the slotted openings 129 orientated at 180° relative to each other. The pairs of openings 129 of the inner distal opening groups 134a, 134b, and 134c are each radially aligned.

Figure 10:
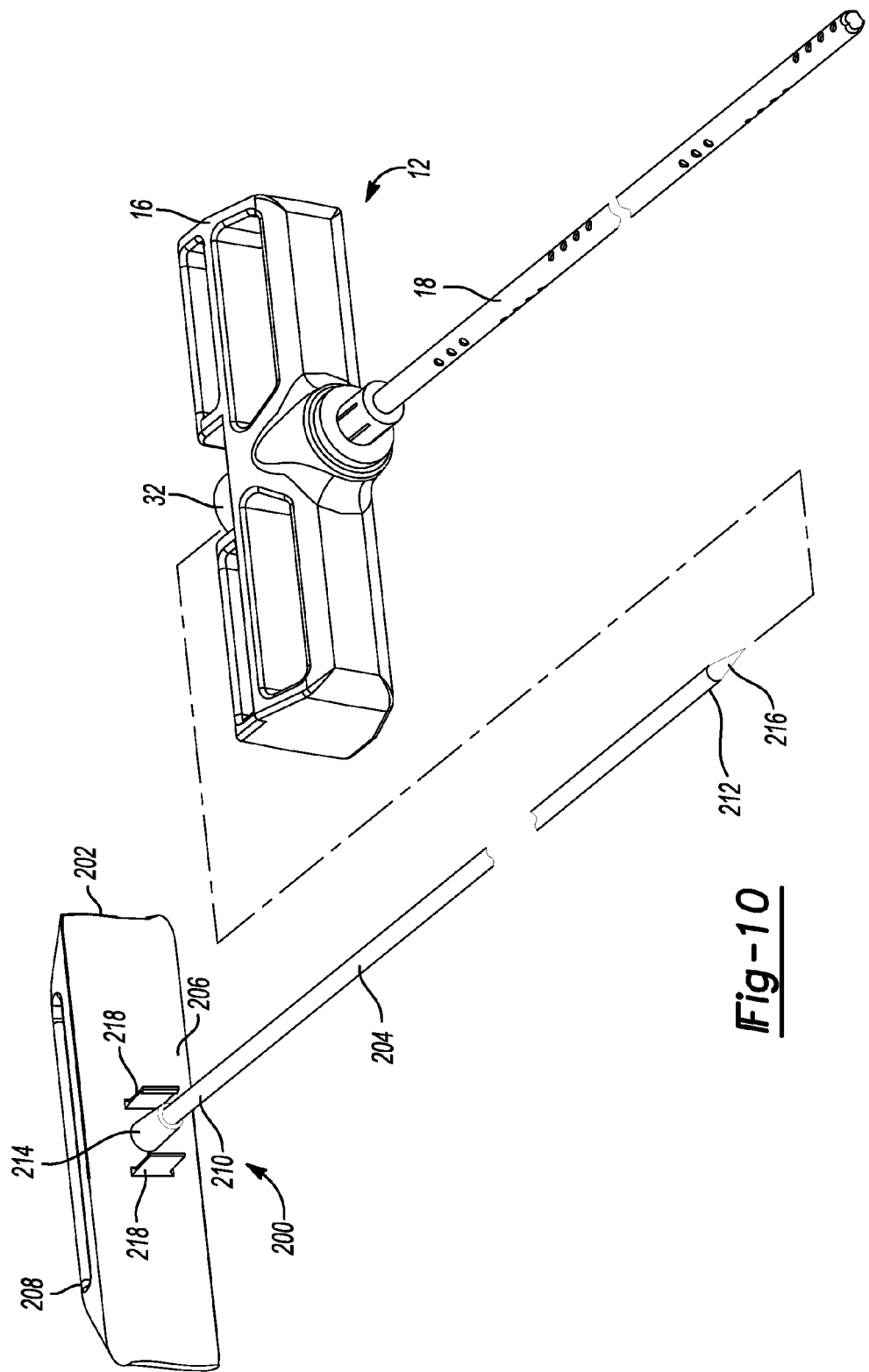
FIG. 10 is a perspective view of a trocar (left side of Figure) configured to be received by the outer needle assembly (right side of Figure)
Figure 11:
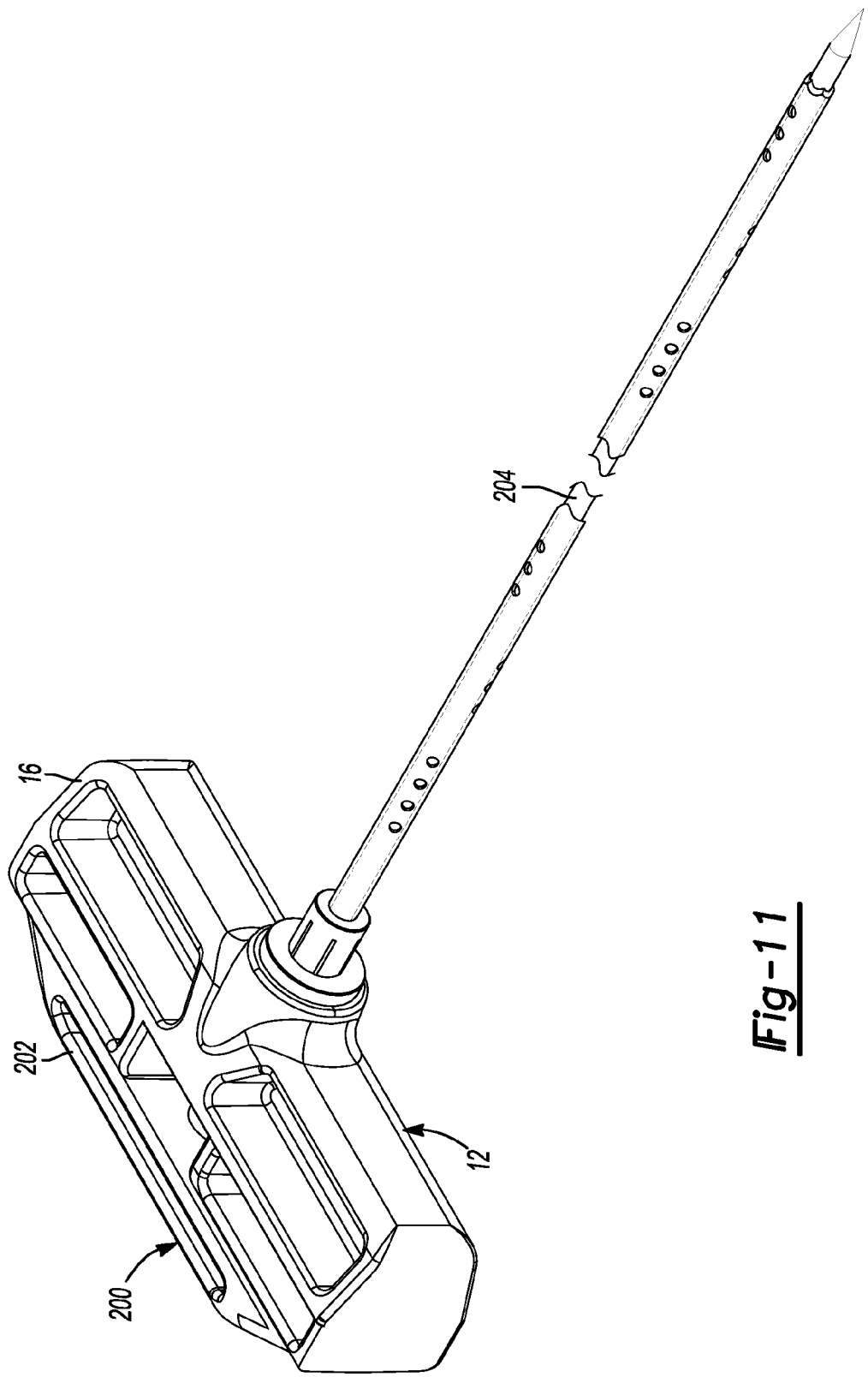
FIG. 11 is an assembled view of the trocar in cooperation with the outer needle assembly.

With additional reference to FIGS. 10 and 11, a trocar is illustrated at reference numeral 200. The trocar 200 generally includes a trocar handle 202 and a trocar needle 204 extending therefrom. The trocar handle 202 includes a distal surface 206 and a proximal surface 208 that is opposite to the distal surface 206. The trocar needle 204 includes a proximal end 210 and a distal end 212. The proximal end 210 is attached to a connector 214 at a center of the distal surface 206 of the trocar handle 202 with a press-fit, for example. The distal end 212 includes a pointed tip 216. The trocar needle 204 is rigid and made from any suitable rigid material, such as a suitable metal. At opposite sides of the connector 214 are locking tabs 218 configured to cooperate with the annular recess 38 of the insert 32 of the outer handle 16 to secure the trocar 200 to the outer handle 16, as further described herein.

With continued reference to FIGS. 1-11 and additional reference to FIGS. 12-19, use of the outer needle assembly 12, the inner needle assembly 14, and the trocar 200 to aspirate bone marrow will now be described. While aspiration of bone marrow from a posterior iliac crest 302 of a pelvis 300 is described, the outer needle assembly 12, the inner needle assembly 14, and the trocar 200 can be used to retrieve/isolate a variety of biological materials from a variety of different sources.

Figure 12:
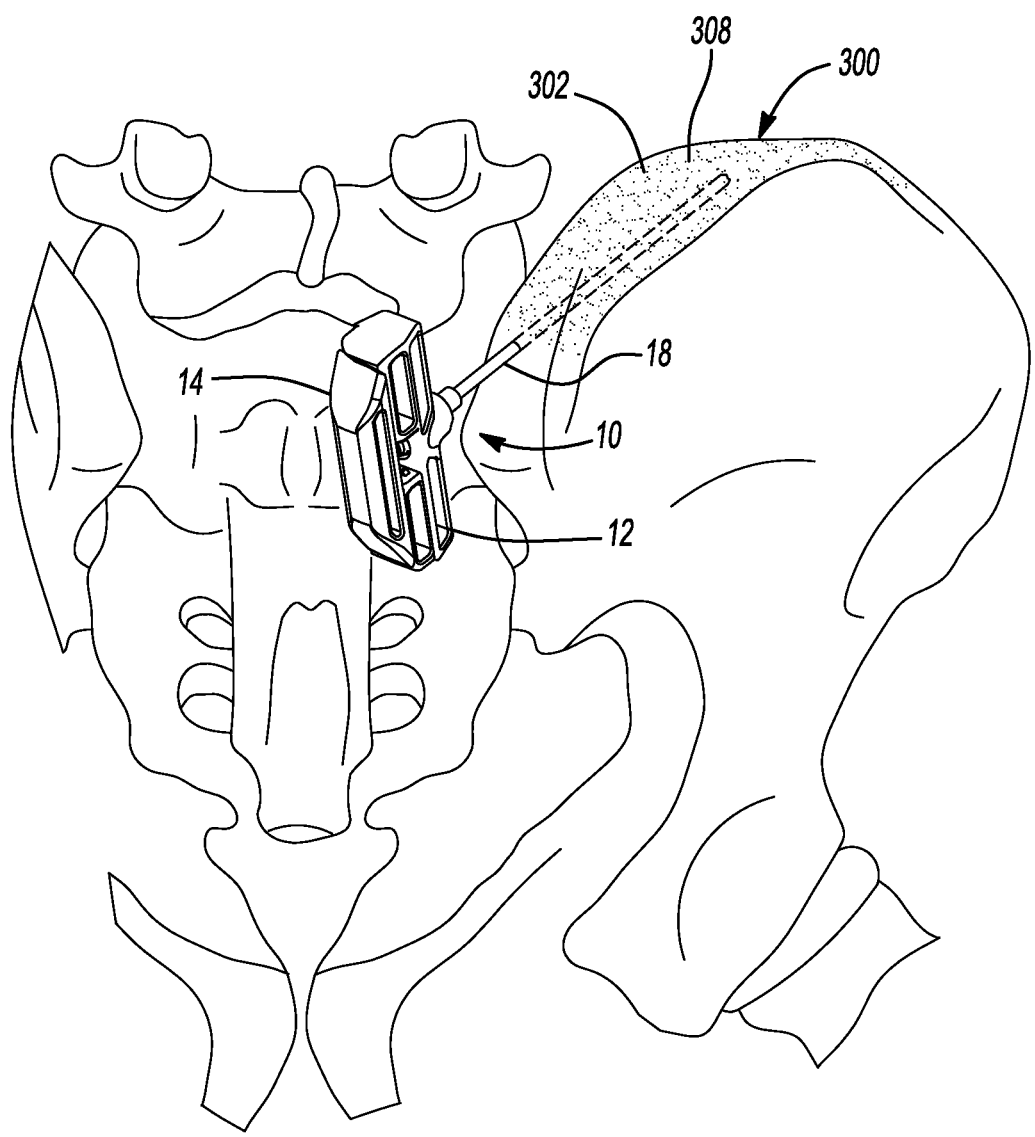
FIG. 12 is a posterior view of a pelvis with the inner cannula and the outer cannula engaging the iliac crest.
Figure 13:
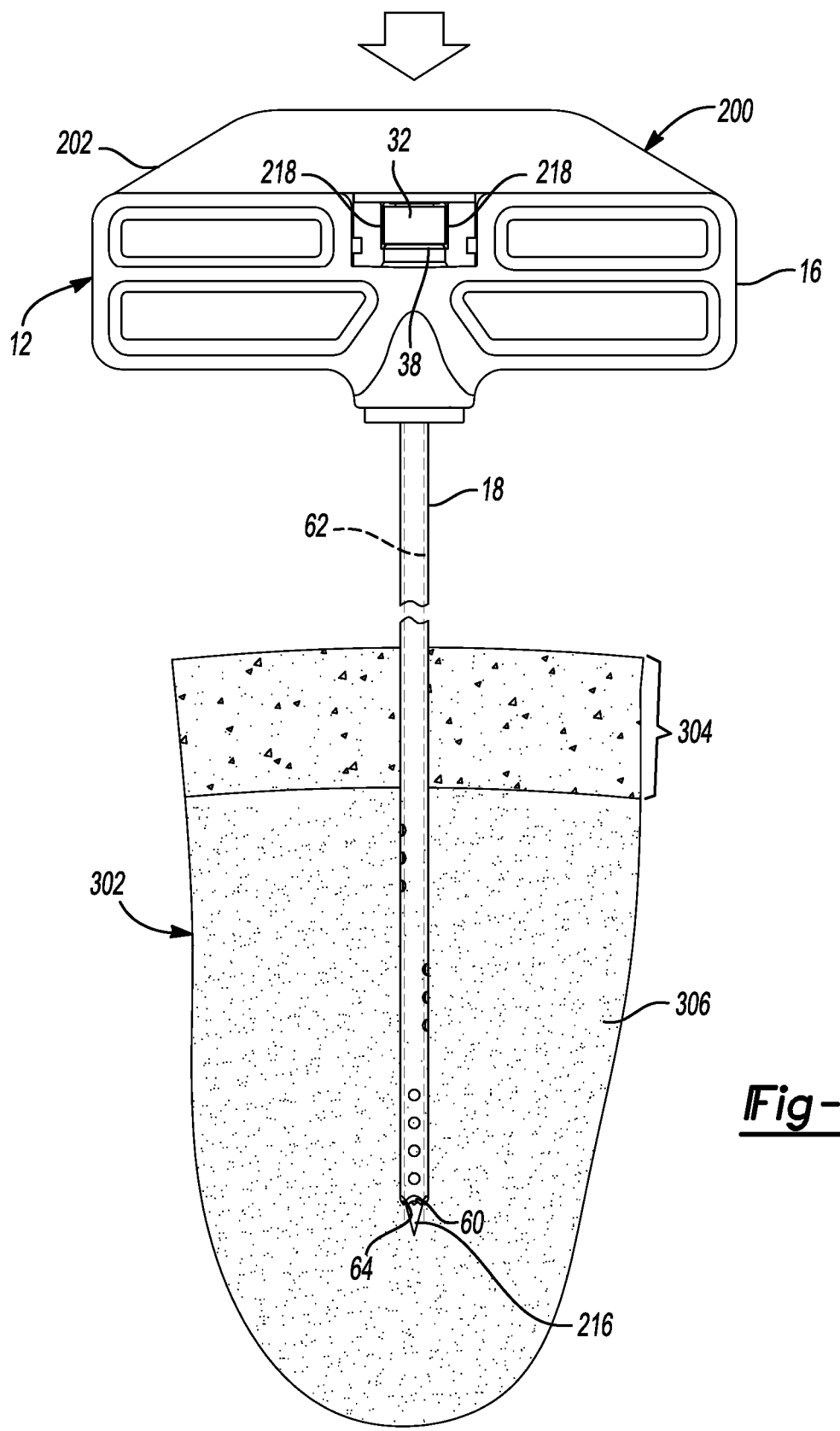
FIG. 13 is a cross-sectional view of the pelvis and illustrates the bone marrow aspiration assembly engaging the pelvis, the assembly including a trocar mounted to the outer needle assembly.

With initial reference to FIGS. 12 and 13, cortical bone 304 and cancellous bone 306 of the iliac crest 302 is initially pierced with a suitable piercing device, such as the trocar 200. As illustrated in FIG. 13, the trocar 200 can be coupled with the outer needle assembly 12 such that the trocar needle 204 extends through the outer cannula passageway 62 and the distal end 212 of the trocar needle 204, including the pointed tip 216, extends beyond the teeth 64 of the distal end 60 of the outer cannula 18. The teeth 64 facilitate piercing and cutting of the cortical bone 304 and the cancellous bone 306 of the iliac crest 302.

The trocar 200 can be secured to the outer needle assembly 12 through cooperation between the locking tabs 218 of the handle 202 and the annular recess 38 of the insert 32 of the outer handle 16. Once the outer cannula 18 is in a desired position and at a desired bone depth within the cancellous bone 306, the trocar 200 can be removed from cooperation with the outer needle assembly 12, which is left in position in the iliac crest 302.

Figure 14:
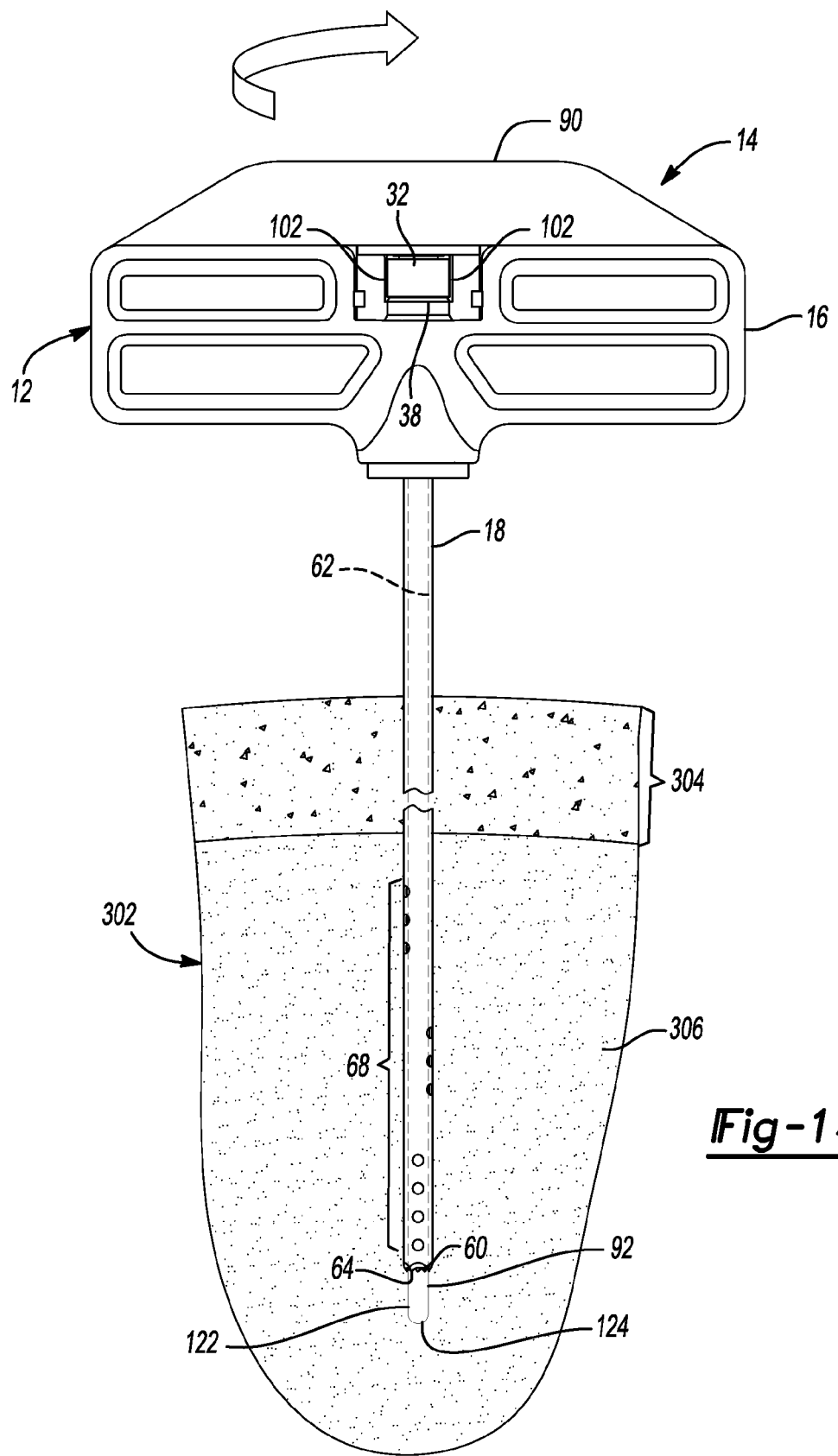
FIG. 14 is a cross-sectional view of the pelvis and illustrates the bone marrow aspiration assembly engaging the pelvis, the assembly including the outer needle assembly and the inner needle assembly.

With reference to FIG. 14, the inner needle assembly 14 is coupled to the outer needle assembly 12 seated in the iliac crest 302 by inserting the inner cannula 92 within the outer cannula 18 such that the distal end 122 of the inner cannula 92, including the closed tip 124, extends beyond the distal end 60 of the outer cannula 18. The connection tabs 102 are coupled to the annular recess 38 of the insert 32 of the outer handle 16 to lock the inner needle assembly 14 to the outer needle assembly 12. The connection cone 100 of the inner cannula handle 90 is seated within the insert 32 such that each of the ridges 106 of the cone 100 are between bumps 50 of each pair of bumps 52, as illustrated in FIG. 15A.

The longitudinal axis A of the outer needle assembly 12 is aligned with the longitudinal axis B when the inner needle assembly 14 is coupled to the outer needle assembly 12, as illustrated in FIGS. 3 and 3A for example. The outer cannula 18 and the inner cannula 92 are arranged such that the outer distal set 68 and the outer proximal set 70 of openings 66 are each aligned along the longitudinal axes A and B with the inner distal set 130 and the inner proximal set 132 of openings 128 respectively.

Figure 15C:
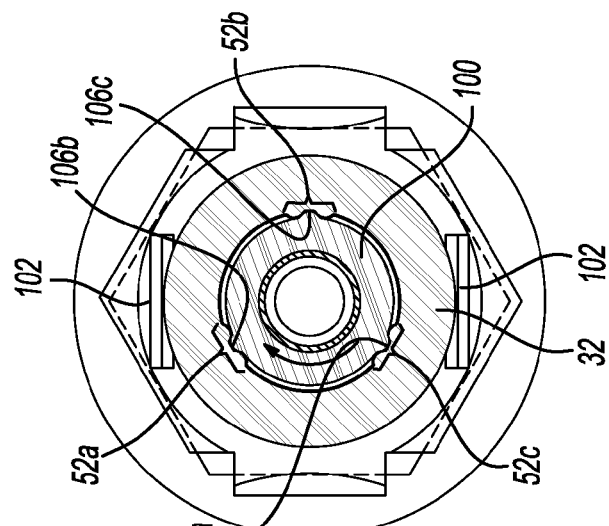
FIG. 15C is a top, cross-sectional view of interaction between the inner needle assembly and the outer needle assembly in a third position.

Because the recess 38 is annular, the inner needle assembly 14 can be rotated with respect to the outer needle assembly 12 about the longitudinal axis A of the outer needle assembly 12, while maintaining alignment of the longitudinal axis A and the longitudinal axis B. The inner needle assembly 14 is generally rotated between a first position (FIG. 15A), a second position (FIG. 15B), and a third position (FIG. 15C).

Figure 15B:
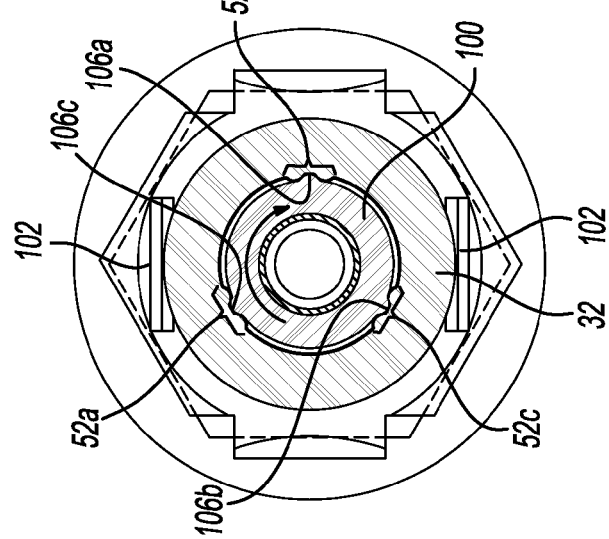
FIG. 15B is a top, cross-sectional view of interaction between the inner needle assembly and the outer needle assembly in a second position.
Figure 15A:
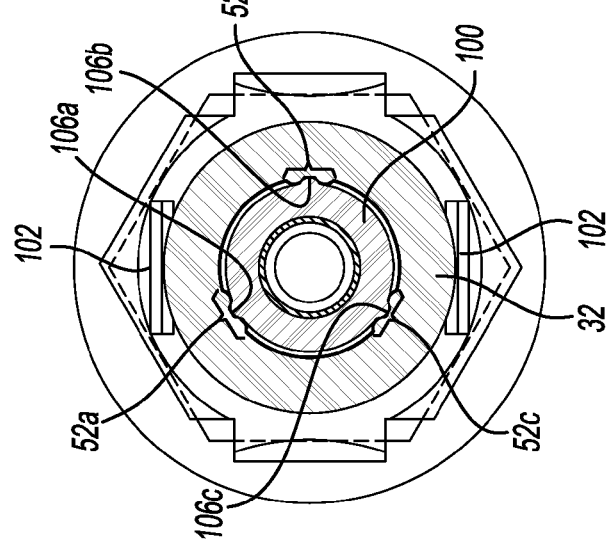
FIG. 15A is a top, cross-sectional view of interaction between the inner needle assembly and the outer needle assembly in a first position.

As illustrated in FIG. 15A, in the first position the first ridge 106a of the connection core 100 is between the bumps 50 of the first pair of bumps 52a, the second ridge 106b is seated between the bumps 50 of the second pair of bumps 52b, and the third ridge 106c is seated between the bumps 50 of the third pair of bumps 52c. Each opening 66 of the outer distal opening group 72a is aligned with an opening 128 of the inner distal opening group 134a. In particular and with reference to FIGS. 16 and 17, the openings 66 of the first and the second outer distal arrays 74a/74b are aligned with the openings 128 of the first and the second inner distal arrays 136a and 136b respectively, thus permitting aspiration of material, such as bone marrow, there through. In contrast, the openings 66 of the outer intermediate and outer proximal arrays 76a, 76b, 78a, and 78b are not aligned with the openings 128 of the inner intermediate and inner proximal arrays 138a, 138b, 140a, and 140b, thus restricting aspiration of bone marrow there through.

Figure 16:
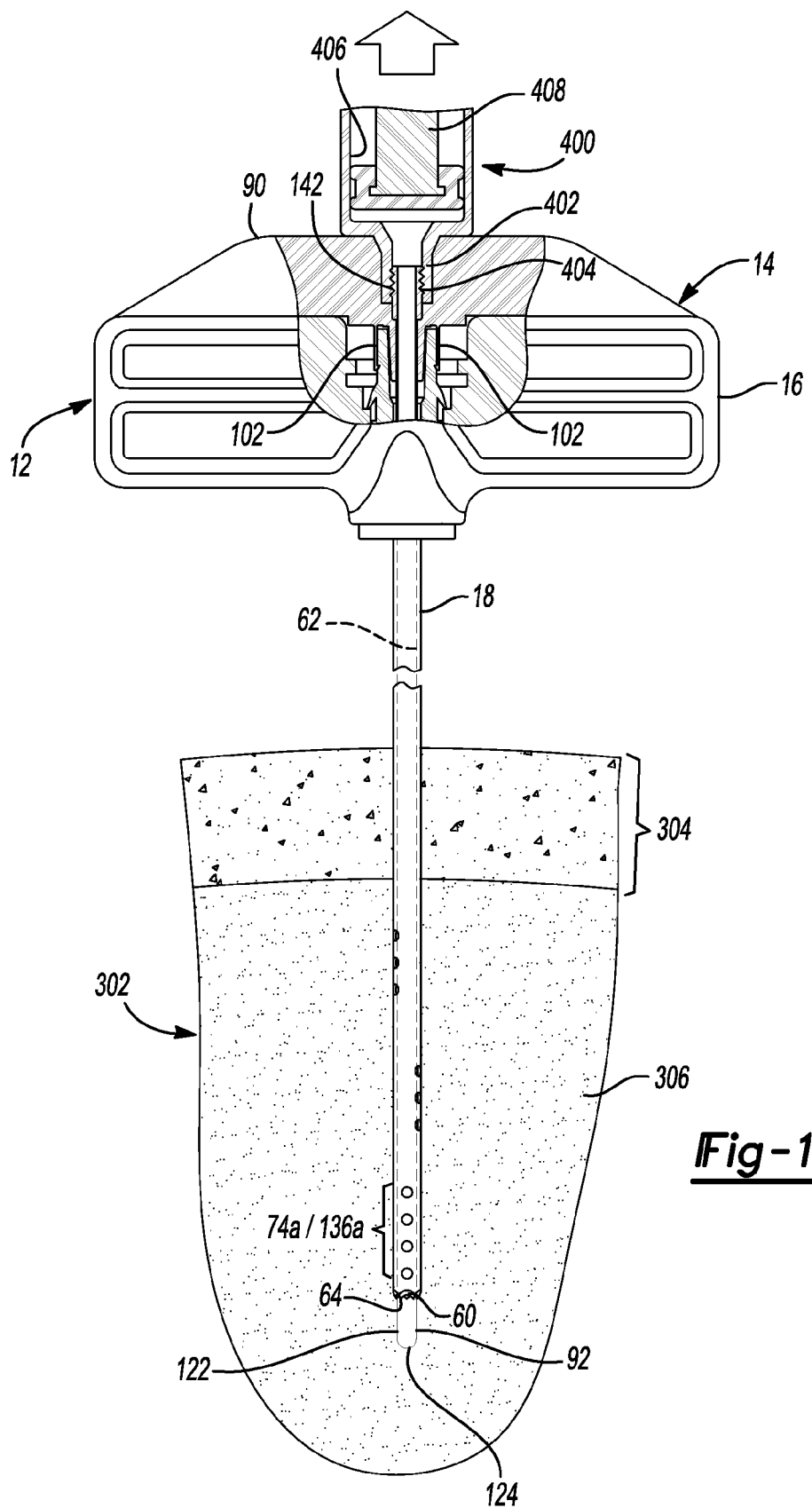
FIG. 16 is a cross-sectional view of the pelvis and the bone marrow aspiration assembly of FIG. 1 in the first position engaging the pelvis, and a syringe for aspirating bone marrow from the pelvis.
Figure 17:
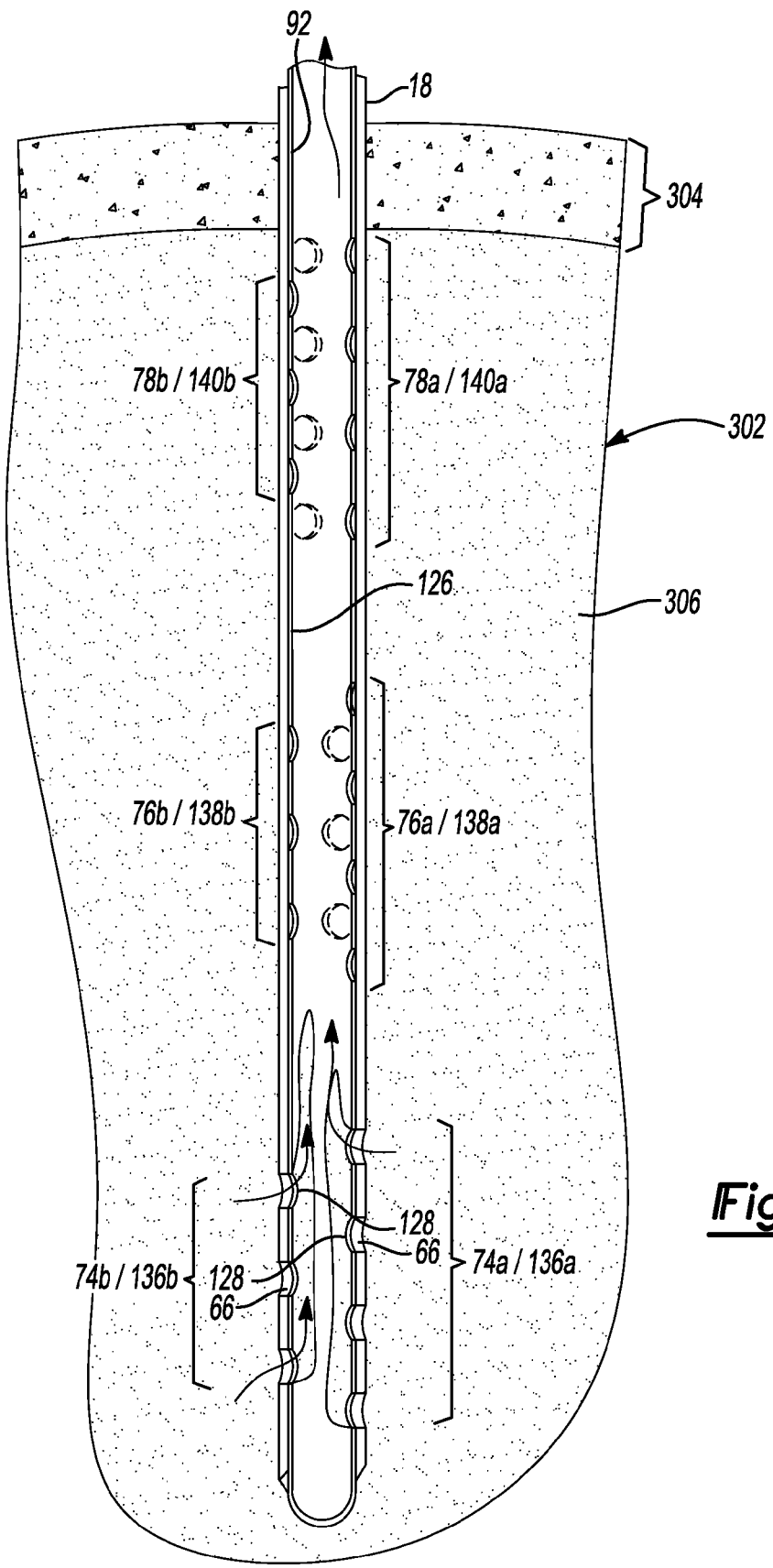
FIG. 17 is a cross-sectional view of the bone marrow aspiration assembly engaging the pelvis with the inner needle assembly and the outer needle assembly each in a first position such that openings of outer and inner distal opening groups are aligned.

With reference to FIG. 16, aspiration is performed using any suitable device, such as a syringe 400. The syringe 400 generally includes a luer lock 402 with threads 404 and a chamber 406 including a plunger 408 (chamber 406 and plunger 408 are conventional features that are partially illustrated). The syringe 400 is connected to the inner handle 90 through cooperation between the threads 404 of the luer lock 402 and the threads 142 at the proximal end 120 of the inner cannula 92. As the plunger 408 is pulled away from the luer lock 402, a negative pressure is established in the chamber 406 and in the passageway 126 of the inner cannula 92, thereby drawing bone marrow through the aligned openings 66 and 128 through the passageway 126 of the inner cannula 92 and into the chamber 406 of the syringe 400. Thus, when the inner needle assembly 14 is in the first position relative to the outer needle assembly 12, bone marrow can be aspirated from an area of the iliac crest 302 that is in close proximity to the outer distal opening group 72a and the inner distal opening group 134a.

Figure 18:
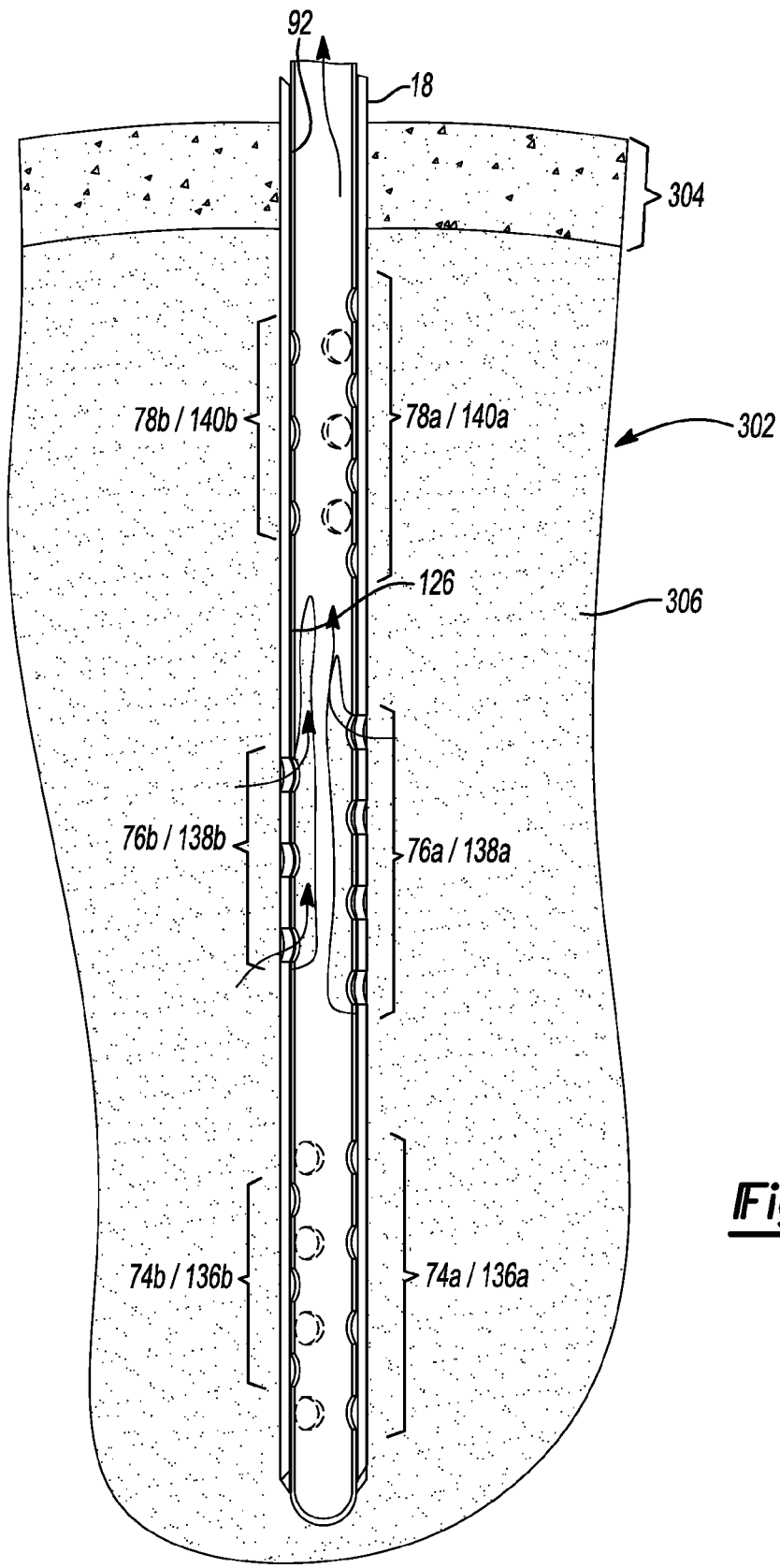
FIG. 18 is a cross-sectional view of the bone marrow aspiration assembly engaging the pelvis with the inner needle assembly and the outer needle assembly each in a second position such that openings of outer and inner intermediate opening groups are aligned.

With reference to FIGS. 15B and 18, to aspirate bone marrow from an area of the iliac crest 302 that is proximate to the outer intermediate opening group 72b and the inner intermediate opening group 134b, the inner needle assembly 14 is rotated 120° about the longitudinal axes A and B from the first position to the second position. In the second position, the first ridge 106a is locked between the bumps 50 of the second pair of bumps 52b, the second ridge 106b is locked between the bumps 50 of the third pair of bumps 52c and the third ridge 106c is locked between the bumps 50 of the first pair of bumps 52a. In this second position, as illustrated in FIG. 18, the openings 66 of the first and the second outer intermediate arrays 76a/76b are aligned with the openings 128 of the first and the second inner intermediate arrays 138a/138b respectively, thus permitting aspiration of material, such as bone marrow, there through. In contrast, the openings 66 of the outer distal and proximal arrays 74a, 74b, 78a, and 78b are not aligned with the openings 128 of the inner distal and proximal arrays 136a, 136b, 140a, 140b, thus restricting aspiration of bone marrow there through.

Figure 19:
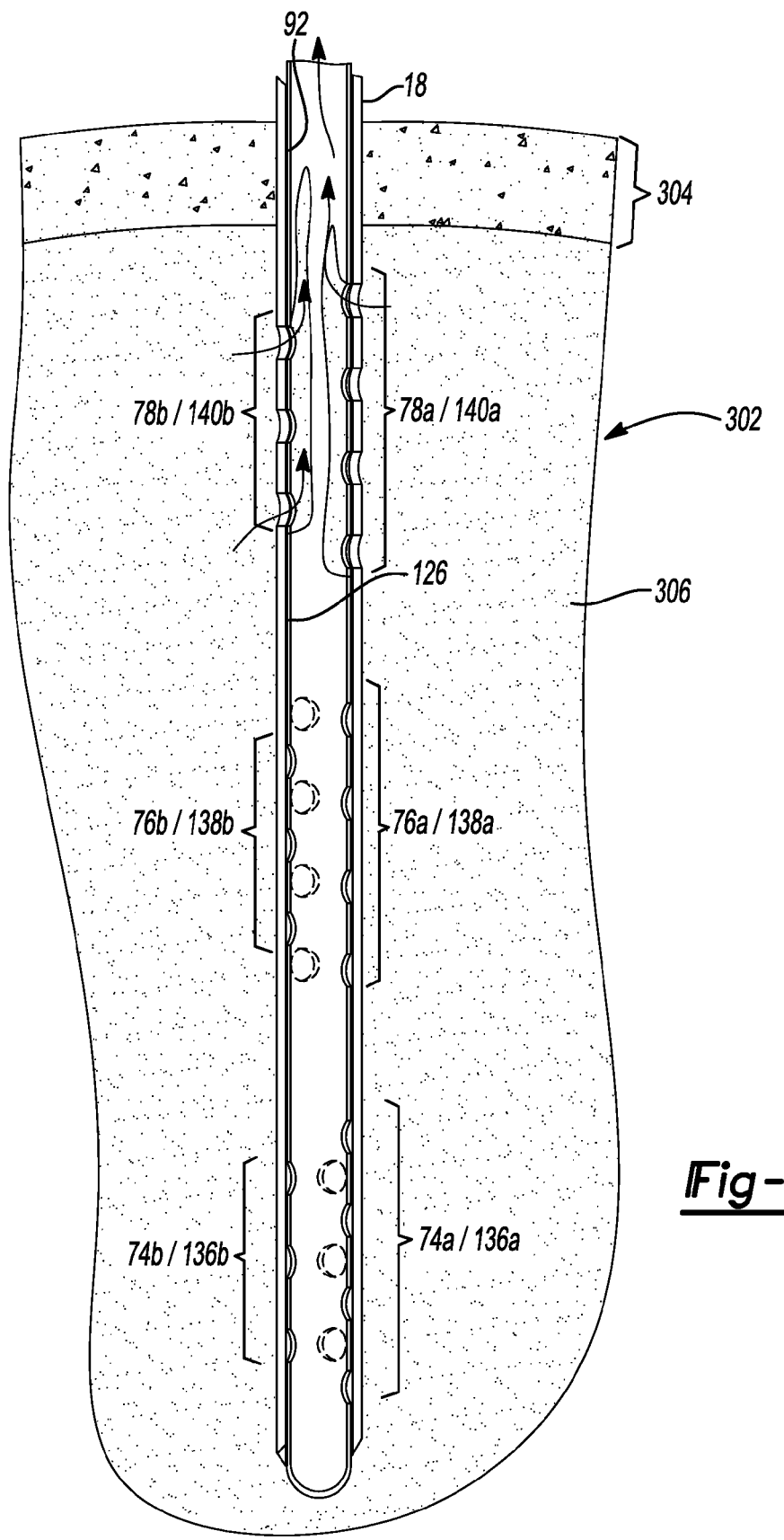
FIG. 19 is a cross-sectional view of the bone marrow aspiration assembly engaging the pelvis with the inner needle assembly and the outer needle assembly each in a third position such that openings of outer and inner proximal opening groups are aligned.

With reference to FIGS. 15c and 19, to aspirate bone marrow from an area of the iliac crest 302 that is proximate to the outer proximal opening group 72c and the inner proximal opening group 134c, the inner needle assembly 14 is rotated 120 degrees about the longitudinal axes A and B from the second position to the third position. In the third position, the first ridge 106a is locked between the bumps 50 of the third pair of bumps 52c, the second ridge 106b is locked between the bumps 50 of the first pair of bumps 52a, and the third ridge 106c is locked between the bumps 50 of the second pair of bumps 52b. In this third position, as illustrated in FIG. 19, the openings 66 of the first and the second outer proximal arrays 78a/78b are aligned with the openings 128 of the first and the second inner proximal arrays 140a/140b respectively, thus permitting aspiration of material, such as bone marrow, there through. In contrast, the openings 66 of the outer distal and intermediate arrays 74a, 74b, 76a, and 76b are not aligned with the openings 128 of the inner distal and intermediate arrays 136a, 136b, 138a, 138b, thus restricting aspiration of bone marrow there through.

The outer proximal set 70 of openings 66 is substantially similar to the outer distal set 68 of openings 66. The inner proximal set 132 of openings 128 is substantially similar to the inner distal set 130 of openings 128. Thus, alignment of the openings 66 and the openings 128 of the outer proximal and inner proximal sets 70 and 132 respectively in each of the first position, the second position, and the third position is the same as the alignment of the openings 66 and 128 of the outer and the inner distal sets 68 and 130 in each of the first, the second, and the third positions.

Thus, cooperation between the outer needle assembly 12 and the inner needle assembly 14 permits aspiration of bone marrow from three different areas of the iliac crest 250. The three different areas are relatively offset both radially and longitudinally without having to move the outer needle assembly 12. Such movement may cause patient discomfort and increase the complexity of the procedure.

Figure 20:
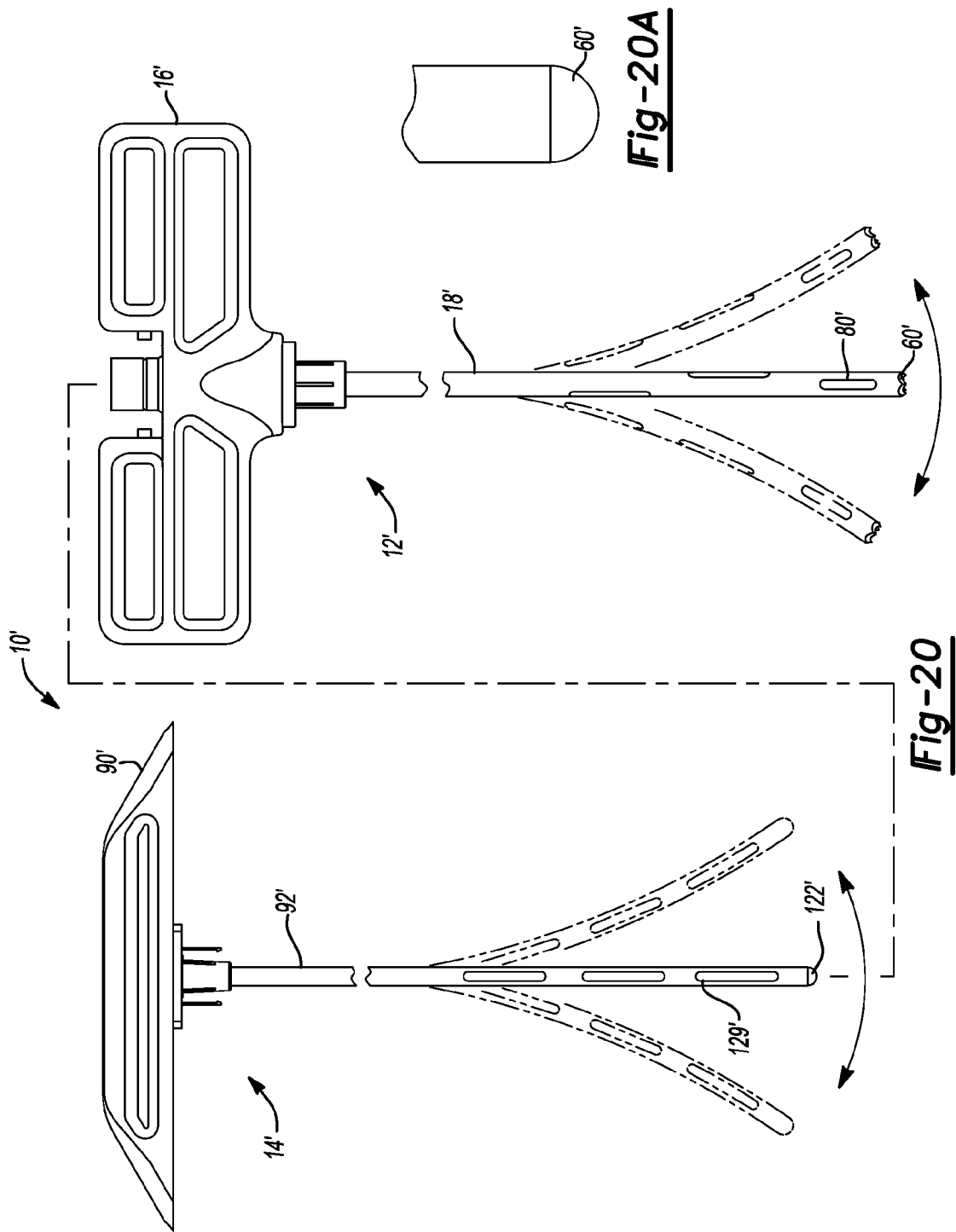
FIG. 20 illustrates an outer needle assembly (right side of Figure) and an inner needle assembly (left side of Figure) of another bone marrow aspiration assembly of the present teachings.

With additional reference to FIG. 20, another bone marrow aspiration assembly according to the present teachings is illustrated at reference numeral 10'. The aspiration assembly 10' is similar to the assembly 10 described above and thus like features are designated with the same reference numerals, but include the prime symbol ('). The assembly 10 generally includes an outer needle assembly 12' including an outer cannula 18' and an inner needle assembly 14' including an inner cannula 92'.

The outer cannula 18' and the inner cannula 92' are both flexible and can be made of any suitable flexible material, such as a suitable polymer or Nitinol. The outer cannula 18' is illustrated as including slots 80' and the inner cannula 92' is illustrated as including slots 129' arranged in the same manner as illustrated in FIG. 8 on the assembly 10 (i.e. proximal, intermediate, and distal groups of slots 80/129 each positioned 120° apart radially). However, the slots 80' and 129' can be provided in any suitable arrangement and/or shape to permit aspiration through selective slots 80' and 129' (or openings 66/128) by rotating the inner cannula 92' with respect to the outer cannula 18'. For example, the slots 80' and 129' can be arranged in two groups of slots 80'/129' positioned 120° apart radially or can have the arrangement of circular openings 66/128 illustrated in, for example, FIGS. 7A and 7B.

Figure 21:
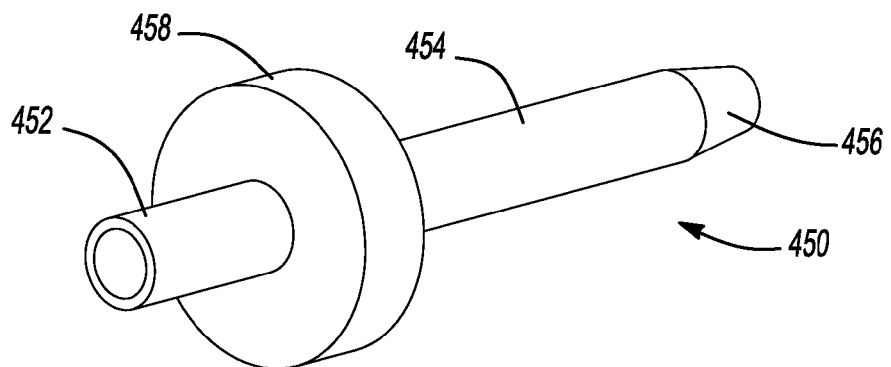
FIG. 21 is a perspective view of a bone piercing needle of the present teachings.

With reference to FIG. 21, a bone piercing needle is illustrated at reference numeral 450. The bone piercing needle 450 includes a head 452, a cannula 454 terminating at an open tip 456, and a collar 458 between the head 452 and the cannula 454. The bone piercing needle 450 is substantially shorter in length than the bone marrow aspiration assembly 10' and is rigid throughout. The cannula 454 is about 3-4 inches in length. The bone piercing needle 450 can be made of any suitable rigid material, such as a metal.

Figure 22:
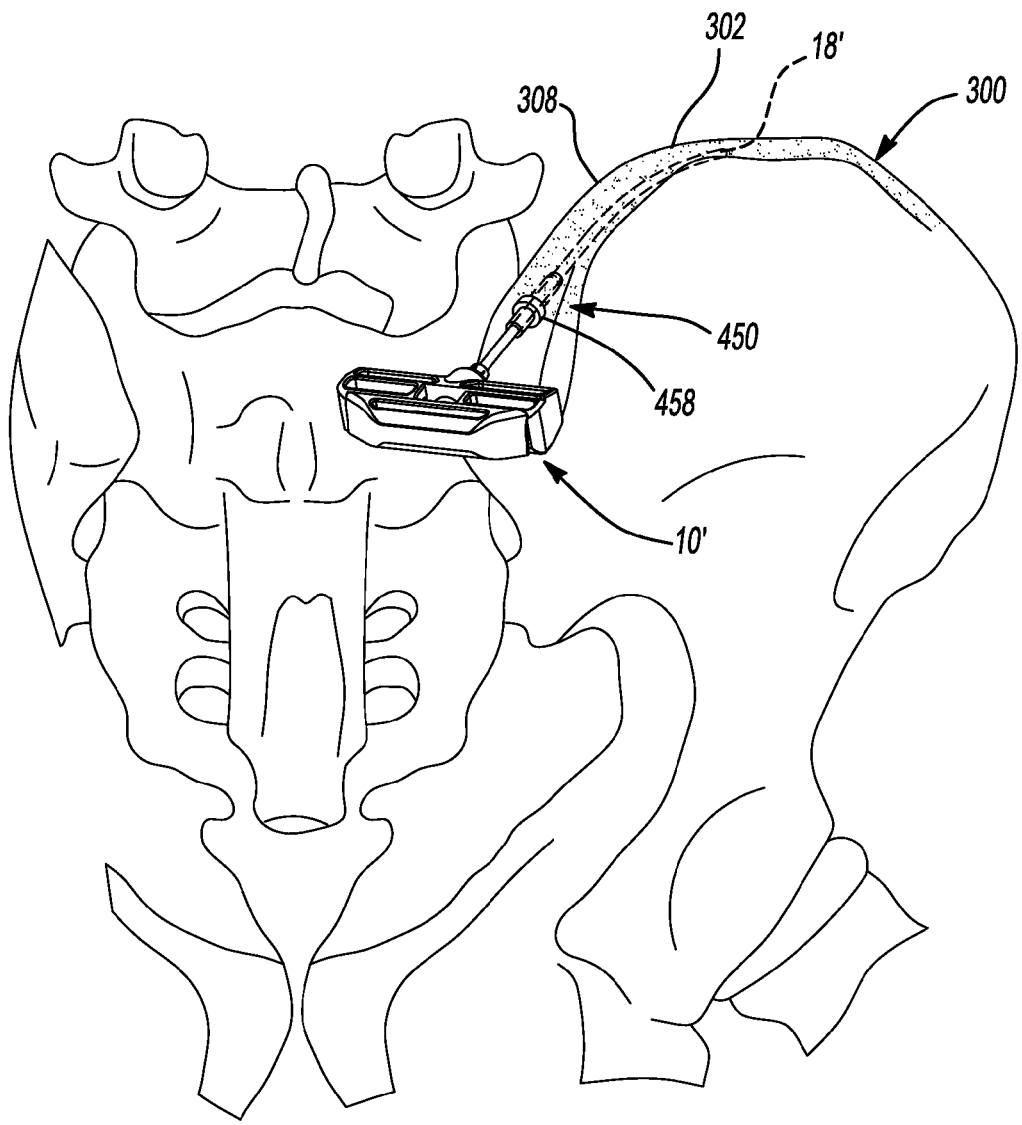
FIG. 22 is a posterior view of a pelvis with the bone piercing needle of FIG. 21 and the bone marrow aspiration assembly of FIG. 20 seated therein.

With additional reference to FIG. 22, use of the bone piercing needle 450 and the aspiration assembly 10' to aspirate bone marrow from the pelvis 300 will now be described. The bone piercing needle 450 is driven into the pelvis 300 such that the collar 458 is at an outer surface of the iliac crest 302 and the cannula 454 extends through the cortical bone 304 to the cancellous bone 306. With the inner needle assembly 14' mated with the outer needle assembly 12', the inner and outer cannulas 18' and 92' are inserted into the iliac crest 302 either through the cannula 454 when the bone piercing needle 450 is left in the pelvis 300 or through the opening created in the pelvis 300 when the bone piercing needle 450 is removed. Because the inner and outer cannulas 18' and 92' are flexible, they are able to track along a curved perimeter 308 of the iliac crest 302, which is typically a rich source of bone marrow. To aspirate bone marrow from the iliac crest 302, a syringe is attached to the assembly 10', which is operated in the same manner as the assembly 10 described above.

The assembly 10' may also include the trocar 200 of FIG. 10, or any other suitable trocar or rigid device, which can be inserted within the outer cannula 18' to facilitate insertion of the outer cannula 18' into the iliac crest 302. The outer cannula 18' may have an open tip 60' as illustrated in FIG. 20, or it may have a closed tip (FIG. 20A). When the tip 60' is open, the trocar 200 may extend beyond the tip 60'.

Figure 23:
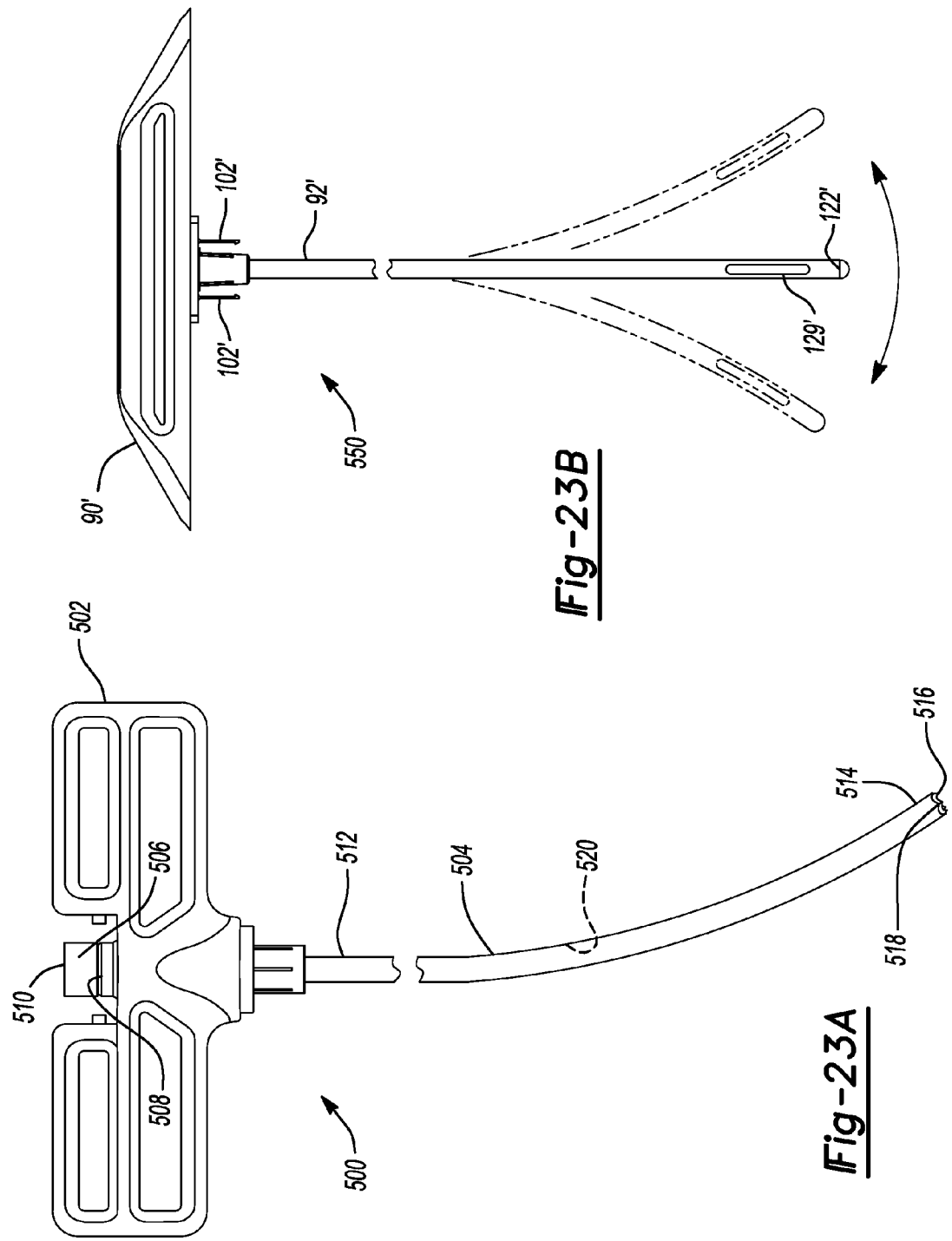
FIG. 23A illustrates a curved introducer needle according to the present teachings.
FIG. 23B illustrates a flexible needle assembly according to the present teachings.

With additional reference to FIG. 23A, an introducer needle is illustrated at reference numeral 500. The introducer needle 500 generally includes a handle 502 and a cannula 504. The handle 502 includes a center connector 506 with an annular recess 508 extending about an exterior surface thereof. The connector 506 includes an opening 510 extending through a center thereof. The opening 510 extends through the handle 502 and is in communication with the cannula 504.

The cannula 504 includes a proximal end 512 secured to the handle 502 and a distal end 514 that is opposite to the proximal end 512. The distal end 514 includes an open tip 516 that may include sharpened edges 518 to facilitate positioning of the of the introducer needle 500 at an implantation site. The cannula 504 defines a channel 520 that extends between the proximal end 512 and the distal end 514. The channel 520 is in cooperation with the opening 510 to provide a continuous passageway through the introducer needle 500.

The cannula 504 is rigid and curved between the proximal end 512 and the distal end 514. The cannula 504 can have any suitable shape and any suitable degree of curvature to match or closely approximate either the overall natural curve of the iliac crest or specific portions thereof to facilitate positioning the cannula 504 proximate to areas with the greatest amount of bone marrow. The cannula 504 can be curved along its entire length or only portions thereof. The cannula 504 can be made of any suitable material, such as a suitable metal. The cannula 504 can optionally include holes along its length in communication with the channel 520, such as the openings 66 or the slots 80 of the outer cannula 18, which can be provided in any suitable size, shape, and arrangement, such as the arrangement herein with respect to the outer cannula 18.

A flexible needle assembly 550 is illustrated in FIG. 23B. The flexible needle assembly 550 is substantially similar to the inner needle assembly 14' and therefore similar features are designated with the same reference numerals, but with the prime (') symbol added. Unlike the inner needle assembly 14', the assembly 550 as illustrated includes only a single pair of slots 129' at the distal end 122', but can include any suitable number of slots 129' or openings (such as openings 128 as arranged in FIGS. 2 and 7A) in any suitable shape, number, or arrangement, such as is provided with the inner needle assembly 14 or 14'.

Figure 24:
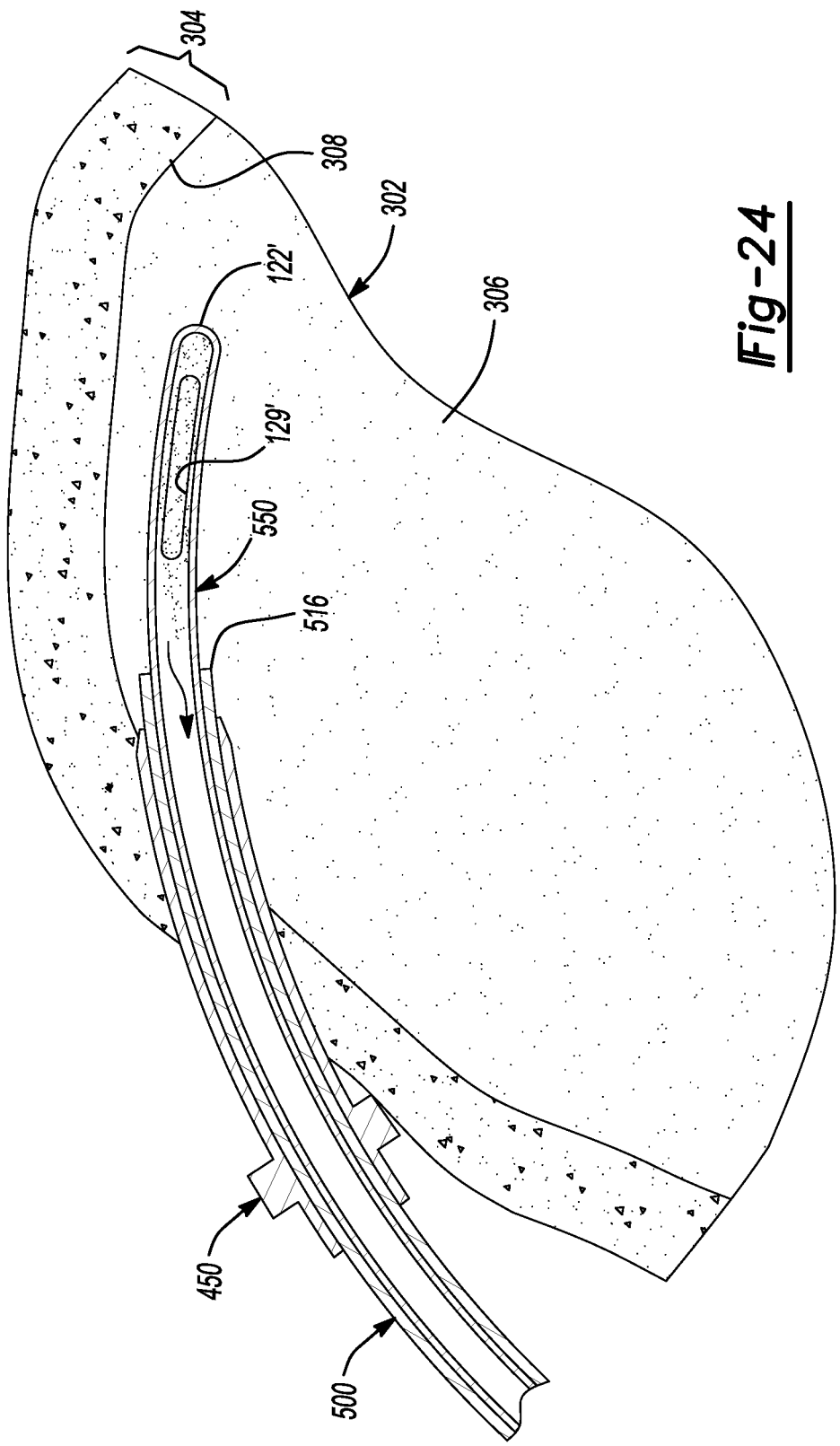
FIG. 24 is a cross-sectional view of the pelvis with the bone piercing needle of FIG. 21, the introducer needle of FIG. 23A, and the flexible needle of FIG. 23B seated therein.

With additional reference to FIG. 24, use of the curved introducer needle 500 to aspirate bone marrow from the iliac crest 302 of the pelvis 300 will now be described. The cortical bone 304 of the iliac crest 302 is initially pierced with the bone piercing needle 450, which is driven within the iliac crest 302 such that the open tip 456 extends to within the cancellous bone 306. The cannula 504 of the introducer needle 500 is then inserted through the cannula 454 of the bone piercing needle 450 and into the iliac crest 302. The bone piercing needle 450 can be curved, as illustrated, to accommodate the introducer needle. The curvature of the cannula 504 is similar to the curvature of the perimeter 308 of the iliac crest 302 and thus the cannula 504 can be positioned proximate to the perimeter 308, an area rich in bone marrow, along at least a majority of its length. Alternatively, the bone piercing needle 450 can be removed prior to insertion of the cannula 504, which can be inserted through the opening in the iliac crest 302 formed by insertion of the cannula 454.

Once the cannula 504 of the introducer needle 500 is at an area of the iliac crest 302 from which bone marrow is to be aspirated, the flexible needle assembly 550 can be mated with the introducer needle 500 such that the tabs 102' are coupled to the annular recess 508 and the inner cannula 92' extends through the channel 520 such that the distal end 122', including a portion with the slots 129' (illustrated as a plurality of circular openings in FIG. 24A), extends beyond the distal end 514. To aspirate bone marrow, a syringe 400 can be coupled to threads of the cannula handle 90' (in a manner substantially similar to that illustrated in FIG. 16) to aspirate bone marrow through the slots 129' of the inner cannula. Alternatively, a syringe can be attached directly to the connector 506 of the introducer needle 500 to aspirate bone marrow directly through the open tip 516. The flexible needle assembly 550 can be rotated to aspirate bone marrow from different areas of the iliac crest 302.

When the cannula 504 includes the slots 80 or the openings 66 of the outer cannula 18 and the cannula 92' includes the slots 129 or the openings 128 of the inner cannula 92, as arranged in FIGS. 7A and 8 for example, bone marrow may be aspirated through select slots 80/129 or openings 66/128 by rotating the flexible needle assembly 550 relative to the cannula 504 to provide selective alignment, and selective aspiration, through the different slots 80/129 or openings 66/128 in the same manner as described in FIGS. 15 and 17-19 with respect to use of the outer needle assembly 12 and the inner needle assembly 14.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A bone marrow aspiration assembly comprising:
an outer cannula extending along a first longitudinal axis, the outer cannula including a first outer surface and a first inner surface, the first inner surface defining a first passageway extending along the first longitudinal axis, the outer cannula defining a plurality of outer openings that are in communication with the first passageway, that extend between the first inner and first outer surfaces of the outer cannula, and are arranged in distal, intermediate, and proximal groups along the first longitudinal axis; and
an inner cannula extending along a second longitudinal axis that is configured to be received in the first passageway, the inner cannula including a second outer surface and a second inner surface, the second inner surface defining a second passageway extending along the second longitudinal axis, the inner cannula defining a plurality of inner openings that are in communication with the second passageway, that extend between the second inner and second outer surfaces of the inner cannula, and are arranged in distal, intermediate, and proximal groups along the second longitudinal axis;
wherein the inner cannula is moved only radially about the second longitudinal axis with respect to the outer cannula to selectively align the inner openings of only one of the distal, intermediate, and proximal opening groups of the inner cannula with the outer openings of only one of the distal, intermediate, and proximal opening groups of the outer cannula to permit aspiration therethrough.

2. The bone marrow aspiration assembly of claim 1, wherein the outer cannula is flexible.

3. The bone marrow aspiration assembly of claim 1, wherein the plurality of outer openings includes a first outer array of first openings that are each radially aligned along the first longitudinal axis, and a second outer array of second openings that are each radially aligned along the first longitudinal axis, the second openings are between the first openings along the first longitudinal axis, the first outer array includes a greater number of openings than the second outer array.

4. The bone marrow aspiration assembly of claim 1, wherein the outer cannula has an open tip and a plurality of teeth spaced apart around a circumference of the tip.

5. The bone marrow aspiration assembly of claim 1, wherein the inner cannula is flexible.

6. The bone marrow aspiration assembly of claim 1, wherein the outer openings are one of circular or elongated slots.

7. The bone marrow aspiration assembly of claim 1,
wherein the distal, intermediate, and proximal groups of the outer openings are radially spaced apart 120° relative to each other about the first longitudinal axis; and
wherein the distal, intermediate, and proximal groups of the inner openings are radially spaced apart 120° relative to each other about the first longitudinal axis.

8. The bone marrow aspiration assembly of claim 7, further comprising:
an outer handle connected to the outer cannula, the outer handle includes a first pair of retention bumps, a second pair of retention bumps, and a third pair of retention bumps spaced apart at 120° intervals; and
an inner handle connected to the inner cannula, the inner handle includes a first retention ridge, a second retention ridge, and a third retention ridge each arranged at 120° intervals and each configured to be retained between one of the first pair, the second pair, and the third pair of retention bumps so as to permit rotation of the inner cannula between a pre-defined first position, a second position, and a third position relative to the outer cannula and the selective alignment of the inner openings and the outer openings such that the inner openings and the outer openings of only the distal opening groups are aligned when the inner cannula is in the first position, the inner openings and the outer openings of only the intermediate opening groups are aligned when the inner cannula is in the second position, and the inner openings and the outer openings of only the proximal opening groups are aligned when the inner cannula is in the third position.

9. The bone marrow aspiration assembly of claim 1, wherein each of the distal, intermediate, and proximal groups of the outer cannula include a first outer array of openings radially spaced apart 180° from a second outer array of openings, each of the first arrays and the second arrays of each of the distal, intermediate, and proximal groups are spaced radially about the first longitudinal axis.

10. The bone marrow aspiration assembly of claim 1, wherein each of the distal, intermediate, and proximal groups of the inner cannula include a first inner array of openings radially spaced apart 180° from a second inner array of openings, the first inner array of openings of each of the distal, intermediate, and proximal groups are radially aligned along the second longitudinal axis, and the second inner array of openings of each of the distal, intermediate, and proximal groups are radially aligned along the second longitudinal axis.

11. A bone marrow aspiration assembly comprising:
a flexible outer cannula defining a first passageway and including a plurality of first ports between a first end and a second end of the first passageway; and
a flexible inner cannula defining a second passageway and configured to be received within the first passageway, the flexible inner cannula includes a plurality of second ports between a first end and a second end of the second passageway;
wherein the flexible inner cannula is longitudinally and axially movable relative to the flexible outer cannula to simultaneously selectively align at least one first port with at least one second port to permit aspiration of bone marrow there through and to misalign at least one first port and at least one second port to restrict aspiration of bone marrow there through; and
wherein the plurality of first ports are arranged in radially spaced apart distal, intermediate, and proximal groups, each group including a plurality of ports extending parallel to a longitudinal axis of the flexible outer cannula.

12. The bone marrow aspiration assembly of claim 11, wherein each of the distal, intermediate, and proximal groups includes a first outer array of ports radially spaced apart 180° from a second outer array of ports, the first arrays of each of the distal, intermediate, and proximal groups are not radially aligned, and the second arrays of each of the distal, intermediate, and proximal groups are not radially aligned.

13. The bone marrow aspiration assembly of claim 12, wherein the plurality of second ports are arranged in distal, intermediate, and proximal groups that each include a first inner array of ports radially spaced apart 180° from a second inner array of ports, the first inner arrays of each of the distal, intermediate, and proximal groups are radially aligned, and the second inner arrays of each of the distal, intermediate, and proximal groups are radially aligned.

14. The bone marrow aspiration assembly of claim 13, wherein each of the first outer arrays include a first plurality of outer ports and each of the second outer arrays include a second plurality of outer ports;
wherein the first plurality of outer ports includes a greater number of ports than the second plurality of outer ports;
wherein each of the first inner arrays include a first plurality of inner ports and each of the second inner arrays include a second plurality of inner ports;
wherein the first plurality of inner ports includes a greater number of ports than the second plurality of inner ports; and
wherein each of the ports are circular.

15. A bone marrow aspiration assembly comprising:
a flexible outer cannula defining a first passageway and including a plurality of first ports between a first end and a second end of the first passageway;
a flexible inner cannula defining a second passageway and configured to be received within the first passageway, the flexible inner cannula includes a plurality of second ports between a first end and a second end of the second passageway; and
a trocar configured to mate with the flexible outer cannula such that a needle of the trocar extends through the entire length of the outer cannula and extends from a distal open tip of the flexible outer cannula;
wherein the flexible inner cannula is longitudinally and axially movable relative to the flexible outer cannula to simultaneously selectively align at least one first port with at least one second port to permit aspiration of bone marrow there through and to misalign at least one first port and at least one second port to restrict aspiration of bone marrow there through; and
wherein the plurality of first ports are arranged in spaced apart distal, intermediate, and proximal groups.

\* \* \* \* \*